US010149925B2

(12) United States Patent
Yamashita et al.

(10) Patent No.: US 10,149,925 B2
(45) Date of Patent: Dec. 11, 2018

(54) METHOD OF REDUCING THE RISK OF EMBOLIZATION OF PERIPHERAL BLOOD VESSELS

(71) Applicant: Terumo Kabushiki Kaisha, Tokyo (JP)

(72) Inventors: Keiko Yamashita, Kanagawa (JP); Shigenori Nozawa, Kanagawa (JP); Katsumi Morimoto, Kanagawa (JP); Kyoko Shimamura, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 252 days.

(21) Appl. No.: 14/457,383

(22) Filed: Aug. 12, 2014

(65) Prior Publication Data

US 2015/0328371 A1 Nov. 19, 2015

Related U.S. Application Data

(63) Continuation of application No. 14/321,282, filed on Jul. 1, 2014, now abandoned.
(Continued)

(51) Int. Cl.
*A61L 29/16* (2006.01)
*A61L 29/14* (2006.01)
(Continued)

(52) U.S. Cl.
CPC ............ *A61L 29/16* (2013.01); *A61K 9/0024* (2013.01); *A61L 29/08* (2013.01); *A61L 29/148* (2013.01);
(Continued)

(58) Field of Classification Search
CPC ........... A61L 2300/415; A61L 2300/63; A61L 2420/06; A61L 29/08; A61L 29/16;
(Continued)

(56) References Cited

U.S. PATENT DOCUMENTS 6,558,405 B1 * 5/2003 McInnes ................. A61F 2/013 606/200
8,597,720 B2 12/2013 Hoffmann et al.
(Continued)

FOREIGN PATENT DOCUMENTS

AU 2014250424 B2 10/2014
EP 0128859 A1 12/1984
(Continued)

OTHER PUBLICATIONS

Schmidt et al., "First Experience With Drug-Eluting Balloons in Infrapopliteal Arteries", Journal of the American College of Cardiology, Sep. 2011, pp. 1105-1109, vol. 58, No. 11.
(Continued)

*Primary Examiner* — Edelmira Bosques
*Assistant Examiner* — Leah Swanson
(74) *Attorney, Agent, or Firm* — Buchanan Ingersoll & Rooney PC

(57) ABSTRACT

A method of reducing the risk of embolization of peripheral blood vessels by providing a medical device having an expandable member having a drug coating layer which has a crystalline morphological form including a plurality of crystal particles of a water-insoluble drug regularly arranged and uniformly sized on the surface of the medical device, inserting the medical device in peripheral blood vessels, expanding the expandable member, pressing the drug coating layer to a blood vessel wall such that at least part of the plurality of crystal particles are transferred to the blood vessel wall, and deflating the expandable member such that the generation of microparticulates having a size that causes embolization of peripheral blood vessels is suppressed.

26 Claims, 13 Drawing Sheets

Related U.S. Application Data

(60) Provisional application No. 61/994,652, filed on May 16, 2014, provisional application No. 61/994,589, filed on May 16, 2014, provisional application No. 61/994,467, filed on May 16, 2014.

(51) Int. Cl.
*A61L 29/08* (2006.01)
*A61L 31/16* (2006.01)
*A61K 9/00* (2006.01)

(52) U.S. Cl.
CPC ............ *A61L 31/16* (2013.01); *A61K 9/0019* (2013.01); *A61L 2300/416* (2013.01); *A61L 2300/63* (2013.01)

(58) Field of Classification Search
CPC ........... A61L 2300/416; A61M 25/104; A61M 2025/105; A61M 25/10; A61M 2025/1075
USPC .......................................................... 604/509
See application file for complete search history.

(56) References Cited

U.S. PATENT DOCUMENTS

| | | | | |
|---|---|---|---|---|
| 2003/0144344 | A1 | 7/2003 | Benigni et al. | |
| 2008/0097301 | A1 | 4/2008 | Alpini et al. | |
| 2008/0097374 | A1 | 4/2008 | Korleski et al. | |
| 2008/0118544 | A1* | 5/2008 | Wang | A61K 31/337 424/423 |
| 2009/0093870 | A1 | 4/2009 | Menendez et al. | |
| 2009/0246252 | A1 | 10/2009 | Arps et al. | |
| 2010/0034960 | A1* | 2/2010 | Kindaichi | A61F 2/91 427/2.25 |
| 2010/0040766 | A1 | 2/2010 | Chappa et al. | |
| 2010/0049296 | A1 | 2/2010 | Sarasam et al. | |
| 2010/0055294 | A1* | 3/2010 | Wang | B05D 1/002 427/2.25 |
| 2010/0104734 | A1* | 4/2010 | Orosa | A61L 31/10 427/2.25 |
| 2010/0209472 | A1 | 8/2010 | Wang | |
| 2010/0272773 | A1 | 10/2010 | Kangas et al. | |
| 2011/0015664 | A1 | 1/2011 | Kangas et al. | |
| 2011/0022027 | A1 | 1/2011 | Morishita et al. | |
| 2011/0099789 | A1 | 5/2011 | Ewing et al. | |
| 2011/0281020 | A1 | 11/2011 | Gong et al. | |
| 2011/0295200 | A1 | 12/2011 | Speck et al. | |
| 2012/0015019 | A1* | 1/2012 | Pacetti | A61K 31/337 424/422 |
| 2012/0100279 | A1 | 4/2012 | Neumann et al. | |
| 2012/0128863 | A1 | 5/2012 | Nguyen et al. | |
| 2013/0142834 | A1 | 6/2013 | Esfand et al. | |
| 2013/0337147 | A1 | 12/2013 | Chappa et al. | |
| 2014/0271775 | A1* | 9/2014 | Cleek | A61L 27/16 424/423 |
| 2014/0328998 | A1 | 11/2014 | Chappa et al. | |
| 2014/0358122 | A1 | 12/2014 | Yamashita et al. | |
| 2015/0328369 | A1 | 11/2015 | Yamashita et al. | |
| 2015/0328372 | A1 | 11/2015 | Yamashita et al. | |
| 2016/0015861 | A1 | 1/2016 | Yamashita et al. | |
| 2016/0310709 | A1 | 10/2016 | Gotou et al. | |
| 2017/0014601 | A1 | 1/2017 | Kurosaki et al. | |
| 2017/0014603 | A1 | 1/2017 | Kurosaki et al. | |
| 2017/0014860 | A1 | 1/2017 | Kurosaki et al. | |
| 2017/0021142 | A1 | 1/2017 | Kurosaki et al. | |

FOREIGN PATENT DOCUMENTS

| | | | |
|---|---|---|---|
| EP | 2 944 334 | A1 | 11/2015 |
| JP | 59-207854 | A | 11/1984 |
| JP | 2005-059225 | A | 3/2005 |
| JP | 2010-509991 | A | 4/2010 |
| JP | 2010-540159 | A | 12/2010 |
| JP | 2012-514510 | A | 6/2012 |
| JP | 2012-533338 | A | 12/2012 |
| JP | 2013-514278 | A | 4/2013 |
| WO | WO 2008/063576 | A2 | 5/2008 |
| WO | WO 2008/063581 | A2 | 5/2008 |
| WO | WO 2009/051614 | A1 | 4/2009 |
| WO | WO 2009/051615 | A1 | 4/2009 |
| WO | WO 2009/051616 | A1 | 4/2009 |
| WO | WO 2009/051618 | A1 | 4/2009 |
| WO | WO 2010/030995 | A2 | 3/2010 |
| WO | WO 2010/079218 | A2 | 7/2010 |
| WO | 2010/124098 | A2 | 10/2010 |
| WO | WO 2011/008393 | A2 | 1/2011 |
| WO | WO 2011/119159 | A1 | 9/2011 |
| WO | WO-2013/181498 | A1 | 12/2013 |
| WO | 2014/152360 | A1 | 9/2014 |
| WO | WO-2014/163091 | A1 | 10/2014 |

OTHER PUBLICATIONS

Yazdani et al., "Vascular, Downstream, and Pharmacokinetic Responses to Treatment with a Low Dose Drug-Coated Balloon in a Swine Femoral Artery Model", Catherization and Cardiovascular Interventions, 2014 (month unknown), pp. 132-140, vol. 83.

Melder et al., "IN.PACT DEB Technology and Pre-clinical Science", Leipzig Interventional Course (LINC), 2013 (month unknown), pp. 1-18.

Virmani, "Pre-clinical safety data and technology review", Leipzig Interventional Course (LINC), 2014 (month unknown), pp. 1-22.

Von Strandmann, "Effect of drug-coated balloon on porcine peripheral arteries: physiologic vascular function, safety and efficacy experiments", Euro PCR, 2013 (month unknown), pp. 1-20.

Joner et al., "Comparative assessment of drug-eluting balloons in an advanced porcine model of coronary restenosis", Thrombosis and Haemostasis, May 2011, pp. 864-872.

Ranger™, "Paclitaxel-Coated PTA Balloon Catheter", Boston Scientific, retrieved on May 16, 2014, pp. 1-6.

Buszman et al., "Tissue Uptake, Distribution, and Healing Response After Delivery of Paclitaxal via Second-Generation Iopromide-Based Balloon Coating", JACC: Cardiovascular Interventions, The American College of Cardiology Foundation, Aug. 2013, pp. 883-890, vol. 6, No. 8.

The extended European Search Report dated Mar. 8, 2017 by the European Patent Office in European Patent Application No. 15709082.0-1455. (7 pages).

The extended European Search Report dated Mar. 8, 2017 by the European Patent Office in European Patent Application No. 15709083.8-1455. (8 pages).

Virmani, "Pros and Cons of Different Technologies in Peripheral Arteries: Insights from a Pathologist", CVPath Institute Inc., pp. 1-41 (exact publication date unknown, but between Jun. 2011 and Jun. 2012).

International Search Report (Form PCT/ISA/210) dated Jun. 17, 2014, by the Japanese Patent Office in International Application No. PCT/JP2014/059665. (5 pages).

Office Action (Patent Examination Report No. 1) dated Dec. 8, 2015, by the Australian Patent Office in Australian Patent Application No. 2014250424. (3 pages).

Gyoengyoesi et al. "TCT-807 Optical Coherence Tomography, Physiologic Vascular Function, Safety and Efficacy Preclinical Studies of Porcine Peripheral Vessels Dilated with Drug-Coated Balloon", (Oct. 29, 2013), JACC vol. 62/18/Suppl B, pp. B245.

U.S. Appl. No. 15/282,230 (U.S. Application No. 2017-0014860), filed Sep. 30, 2016.

U.S. Appl. No. 15/282,087 (U.S. Application Publication No. 2017-0014601), filed Sep. 30, 2016.

U.S. Appl. No. 15/281,860 (U.S. Application Publication No. 2017-0014603), filed Sep. 30, 2016.

U.S. Appl. No. 15/282,563 (U.S. Application Publication No. 2017-0021142), filed Sep. 30, 2016.

Office Action issued by the Canadian Intellectual Property Office in corresponding Canadian Patent Application No. 2,908,420 dated Jan. 26, 2017 (4 pages).

(56) References Cited

OTHER PUBLICATIONS

Extended Search Report issued by the European Patent Ofgfice in corresponding European Patent Application No. 14779028.1 dated Jan. 25, 2017 (11 pages).
Extended Search Report issued by the European Patent Office in related European Patent Application No. 15709081.2 dated Mar. 8, 2017 (6 pages).
International Search Report (PCT/ISA/210) dated Jun. 16, 2015, by the Japanese Patent Office as the International Searching Authority for International Application No. PCT/JP2015/058546.
Written Opinion (PCT/ISA/237) dated Jun. 16, 2015, by the Japanese Patent Office as the International Searching Authority for International Application No. PCT/JP2015/058546.
International Search Report (PCT/ISA/210) dated Jun. 16, 2015, by the Japanese Patent Office as the International Searching Authority for International Application No. PCT/JP2015/058547.
Written Opinion (PCT/ISA/237) dated Jun. 16, 2015, by the Japanese Patent Office as the International Searching Authority for International Application No. PCT/JP2015/058547.
International Search Report (PCT/ISA/210) dated Aug. 4, 2015, by the Japanese Patent Office as the International Searching Authority for International Application No. PCT/JP2015/058548.
Written Opinion (PCT/ISA/237) dated Aug. 4, 2015, by the Japanese Patent Office as the International Searching Authority for International Application No. PCT/JP2015/058548.
Poletto et al. "Characterization of Polyamide 66 Membranes Prepared by Phase Inversion using Formic Acid and Hydrochloric Acid Such as Solvents", May 5, 2011, 14(4), pp. 547-551.
Office Action issued by the Australian Patent Office dated Dec. 21, 2017 in Australian Patent Application No. 2015260675 (3 pages).
U.S. Appl. No. 15/881,050, filed Jan. 26, 2018, Kurosaki et al.

* cited by examiner

10

C6-b

METHOD OF REDUCING THE RISK OF EMBOLIZATION OF PERIPHERAL BLOOD VESSELS

RELATED APPLICATIONS

This application is a continuation of U.S. application Ser. No. 14/321,282, filed on Jul. 1, 2014, which claims the benefit of U.S. Provisional Application Nos. 61/994,652, 61/994,589 and 61/994,467, all filed on May 16, 2014, the contents of which are hereby incorporated by reference.

TECHNICAL FIELD

Disclosed is a drug coating layer of water-insoluble drugs, and a drug coating layer exhibiting a specific crystalline morphological form of the water-insoluble drugs, and a method of reducing the risk of embolization of peripheral blood vessels.

BACKGROUND DISCUSSION

In recent years, development of a drug eluting balloon (DEB) in which a balloon catheter is coated with drugs has been actively performed, and it has been reported to be effective in the treatment and prevention of restenosis. The balloon is coated by a coating film including drugs and excipients, and when a blood vessel is dilated, the balloon presses against a blood vessel wall, and it delivers the drugs to target tissue.

In recent years, it has been found that a morphological form of the drugs coated on the balloon surface influences releasing property and tissue transferability of drugs from the balloon surface in a lesion affected area, and it is known that control of the crystal form or amorphous form of drugs is important.

Since it cannot be said that the drug eluting balloon having a coating layer in the related art sufficiently exhibits low toxicity and a high effect on a stenosis inhibition rate when treating a stenosis portion in a blood vessel, a medical device of which the toxicity is even lower and the stenosis inhibiting effect is high is desired.

DEB has an advantage of use because DEB does not leave any foreign bodies in the blood vessels, unlike BMS (bare metal stent) and DES (drug-eluting stent). In particular, although use of stents is not recommended in the treatment of lower limbs, a demand for DEB is required. Meanwhile, a risk for the embolization of downstream peripheral blood vessels is feared which is caused by microparticulates upon use of DEB. Since embolization of peripheral blood vessels could cause a risk of amputation of lower limbs due to necrosis, alleviation of embolization of peripheral blood vessels is clinically significant. The blood vessels in the BTK (below-the-knee) area are positioned to the peripheral, and the diameter of the blood vessels is small. Therefore a risk for the embolization is focused on and DEB is required to have a lower risk of the embolization. It is presumed that this is relevant not only to the number of the microparticulates, but also the size of microparticulates. The larger the size is, the more possibility the microparticulates are distributed in the muscles adjacent downstream peripheral blood vessels. It is thought that this raises the risk of the embolization, and the size of the microparticulates is expected to be small.

To obtain sufficient treatment effects of DEB, it is important to keep the drug concentration to be transferred to the lesion of the vascular tissue and chronological transition of drug concentration. Further, in the initial term to inhibit the proliferation of smooth muscle cells, relatively high drug concentration is necessary in the vascular tissue, although in the final term to non-inhibit endothelial cells growth, prompt clearance of drug from the tissue is required. When these two points are achieved by DEB in terms of a change of drug concentration, DEB can provide superior treatment effects in both efficacy and safety.

One of the features of DEB is to immediately release drug upon the dilation of the balloon in a couple of minutes and to transfer a sufficient amount of the drug to the vascular tissue. If the drug is not transferred uniformly to the entire treated lesion, uniform inhibitory effects cannot be expected to be imparted to the lesion under treatment. Particularly, since the length of lesion in the blood vessels of lower limbs is longer than that of coronary arteries, it is difficult to obtain uniform efficacy in lower limbs.

SUMMARY

A challenge in the art is to provide a drug coating layer having a morphological form of water-insoluble drugs of which the intravascular stenosis inhibitory effect in a lesion affected area is high, when delivering medical device coated with a drug into the body and medical device using the same.

The challenge is addressed by a drug coating layer having a specific crystalline morphological form of a water-insoluble drug which has a high intravascular stenosis inhibitory effect in a lesion affected area.

Various aspects are disclosed as follows:

(1) A drug coating layer which has a morphological form including a plurality of elongated bodies with long axes that each crystal of a water-insoluble drug independently has, on a substrate surface, in which the long axes of the elongated bodies are nearly linear in shape, and the long axes of the elongated bodies form an angle in a predetermined range, preferably an angle in a range of 45° to 135°, with respect to a substrate plane with which the long axis of the elongated body intersects.

(2) The drug coating layer described in (1) in which at least near the distal of the elongated body is hollow.

(3) The drug coating layer described in (1) or (2) in which a cross-sectional shape of the elongated body on a surface perpendicular to the long axis is a polygon.

(4) The drug coating layer which is a drug coating layer in which crystals of a flatly elongated hair-like shape of crystals of the water-insoluble drug are randomly laminated on the substrate surface, and in which the long axes of some of the crystals have a portion curved in shape, and crystals having other shapes are not mixed in the same crystal plane.

(5) The drug coating layer described in (4) in which the surface of the crystal of the water-insoluble drug is covered with an amorphous film.

(6) The drug coating layer including a crystalline morphological form of the water-insoluble drug, crystal particles of the water-insoluble drug arranged with regularity on the substrate surface, and excipient particles formed of an excipient irregularly arranged between the crystal particles, wherein a molecular weight of the excipient is less than a molecular weight of the water-insoluble drug, a ratio occupied by the excipient particles per a predetermined area of the substrate is less than a ratio occupied by the crystal particles, and the excipient particles do not form a matrix.

(7) The drug coating layer described in any one of (1) to (6) in which the water-insoluble drug is rapamycin, paclitaxel, docetaxel, or everolimus.

(8) Medical device having the drug coating layer described in any one of (1) to (7) on the surface of the medical device, which is reduced in diameter to be delivered when delivered into a body, and enlarged in diameter to release a drug from the drug coating layer at an affected part.

(9) A method for delivering a drug having a step of delivering the medical device described in (8) to a lumen, a step of radially dilating a dilatable portion provided in the medical device, and a step in which the drug coating layer which has the dilatable portion is applied to the lumen.

A drug coating layer for drug eluting medical device can be provided of which the intravascular stenosis inhibitory effect in a lesion affected area is high and/or the toxicity is low.

A method is provided for reducing the risk of embolization of peripheral blood vessels, comprising providing a medical device having an expandable member having a drug coating layer which has a crystalline morphological form including a plurality of crystal particles of a water-insoluble drug regularly arranged and uniformly sized on the surface of the medical device, inserting the medical device in peripheral blood vessels, expanding the expandable member, pressing the drug coating layer to the blood vessel wall such that at least part of the plurality of crystal particles are transferred to the blood vessel wall, and deflating the expandable member such that the generation microparticulates having a size that causes embolization of peripheral blood vessels is suppressed.

A method is provided for treating peripheral artery diseases in lower limbs, comprising providing a medical device having an expandable member having a drug coating layer which has a crystalline morphological form including a plurality of crystal particles of a water-insoluble drug regularly arranged and uniformly sized on the surface of the medical device, inserting the medical device in peripheral blood vessels, expanding the expandable member, pressing the drug coating layer to the blood vessel wall such that at least part of the plurality of crystals are transferred to the blood vessel wall, and deflating the expandable member such that a pharmacokinetics profile is presented in which a drug concentration in the blood vessels is kept for the inhibition of smooth muscle cell proliferation in a high drug-concentration period of time, and for the non-inhibition of endothelial cell growth in a later low drug-concentration period of time.

A method is provided for inhibiting thickening of vascular intima, comprising providing a medical device having an expandable member having a drug coating layer which has a crystalline morphological form including a plurality of crystal particles of a water-insoluble drug regularly arranged and uniformly sized on the surface of the medical device, inserting the medical device in peripheral blood vessels, expanding the expandable member, pressing the drug coating layer to a blood vessel wall such that at least part of the plurality of crystals are transferred to the blood vessel wall, and deflating the expandable member such that a vascular intima thickening is inhibited uniformly in an entire treated lesion (entire long lesion) of stenosis to uniformly cause patency of the lesion.

BRIEF DESCRIPTION OF THE DRAWINGS

FIG. 1A is a SEM image at 2,000 times magnification of crystals observed on a substrate surface of the drug coating layer prepared in Example 1. FIG. 1B is a SEM image at 1,000 times magnification of crystals observed on another portion of a substrate surface prepared in Example 1. FIG. 1C is a SEM image at 400 times magnification of crystals observed on another portion of the substrate surface prepared in Example 1. FIG. 1D is a SEM image at 4,000 times magnification of crystals observed at a cross-section perpendicular to the substrate surface of the drug coating layer prepared in Example 1.

DETAILED DESCRIPTION

Figure 1A:
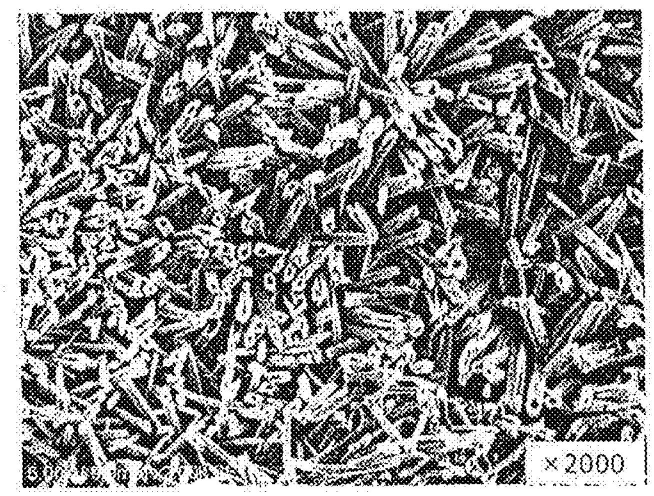
FIGS. 1A to 1D are diagrams showing a scanning electron microscopic image (hereinafter, referred to as SEM) of a surface of a drug coating layer prepared in Example 1.
Figure 1B:
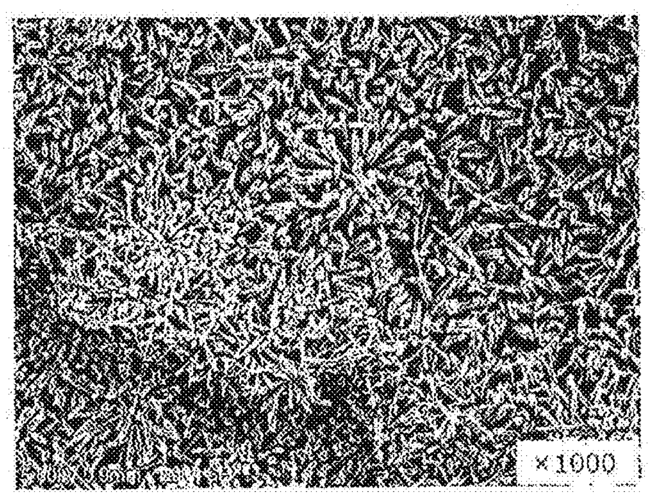
Figure 1C:
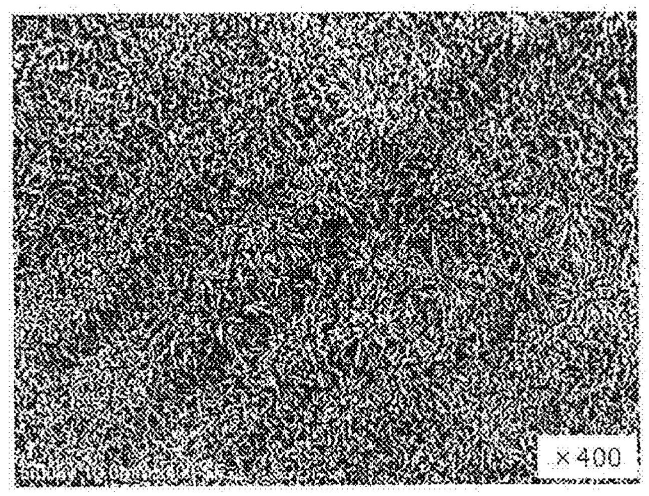
Figure 1D:
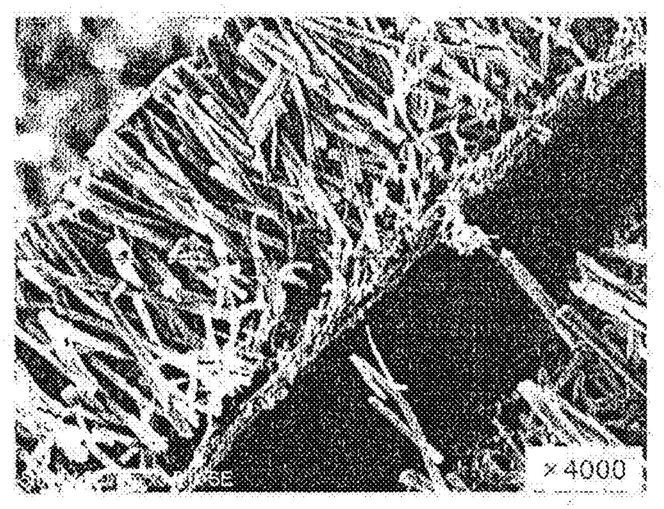
Figure 2:
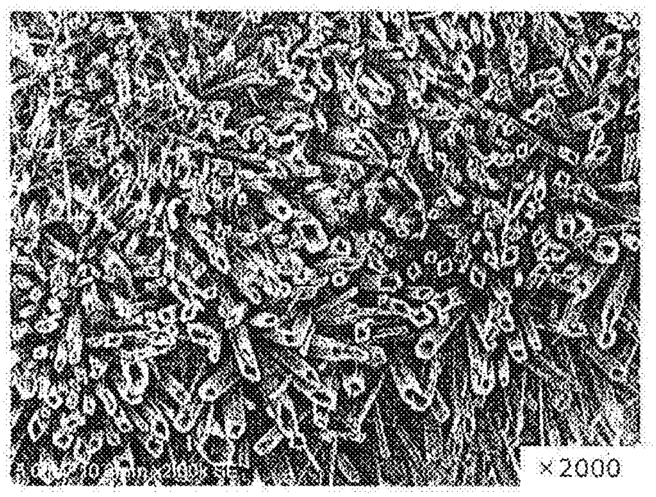
FIG. 2 is a diagram showing a SEM image at 2,000 times magnification of crystals observed on the substrate surface of the drug coating layer prepared in Example 2.
Figure 3A:
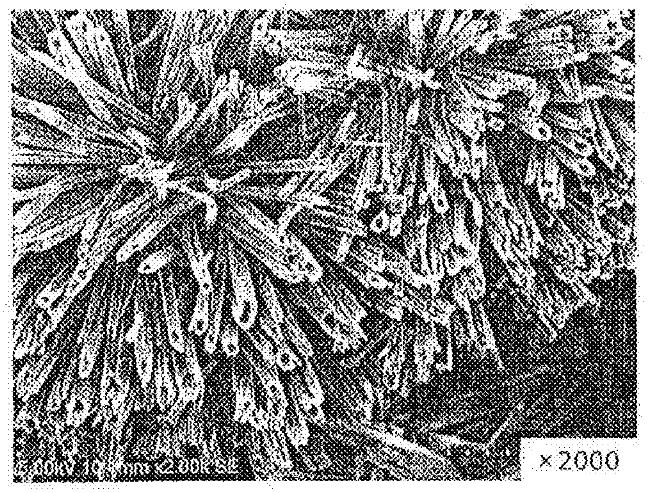
FIG. 3A is a diagram showing a SEM image at 2,000 times magnification of crystals observed on the substrate surface of the drug coating layer prepared in Example 3.
Figure 3B:
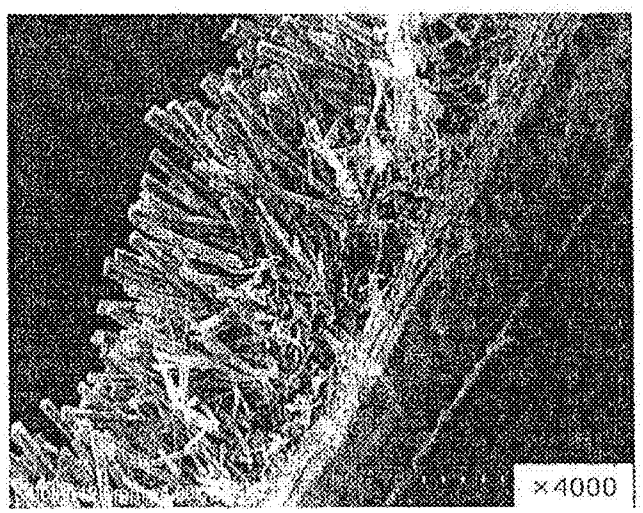
FIG. 3B is a SEM image at 4,000 times magnification of crystals observed at a cross-section perpendicular to the substrate surface of the drug coating layer prepared in Example 3.
Figure 4:
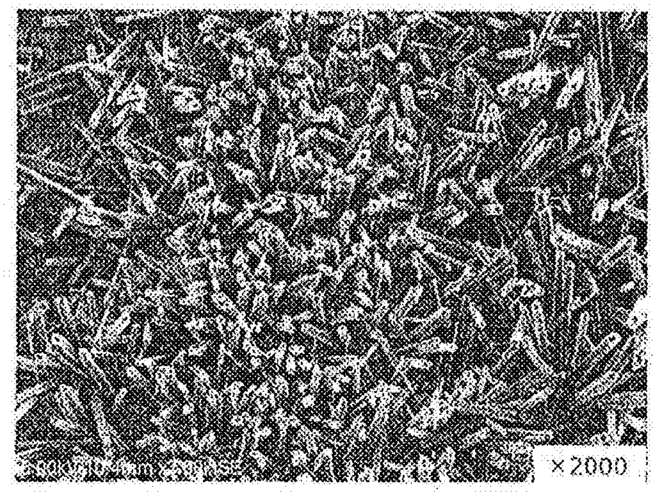
FIG. 4 is a diagram showing a SEM image at 2,000 times magnification of crystals observed on the substrate surface of the drug coating layer prepared in Example 4.
Figure 5:
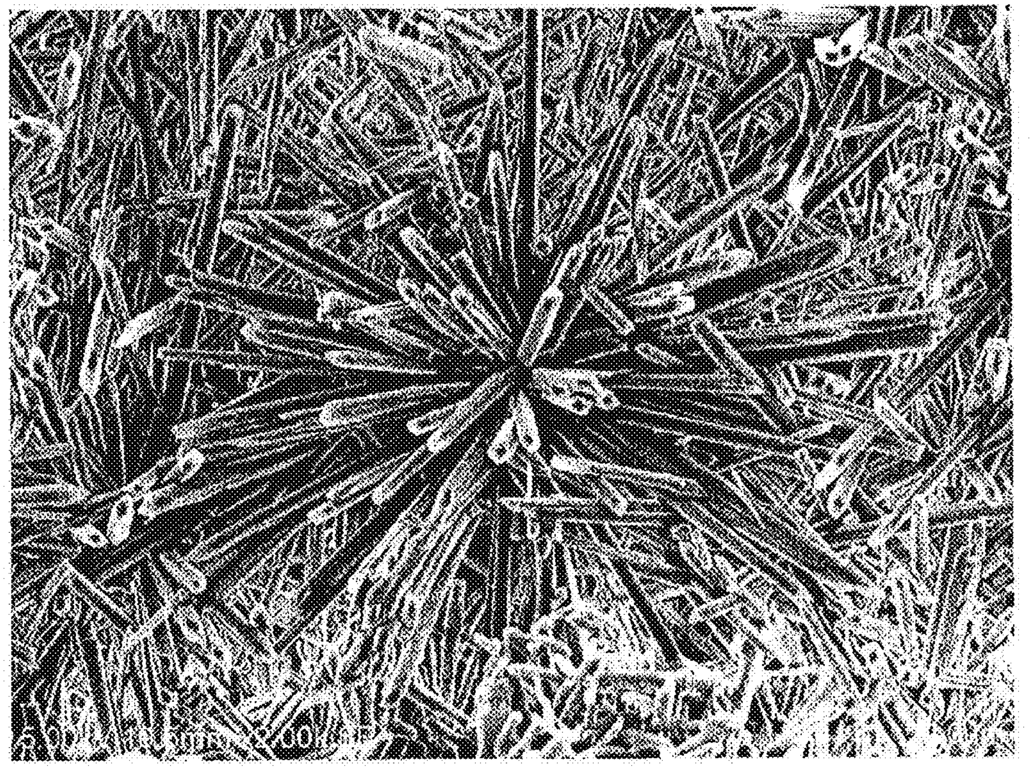
FIG. 5 is a diagram showing a SEM image at 2,000 times magnification of crystals observed on the substrate surface of the drug coating layer prepared in Example 5.

It has been determined that a drug coating layer having low toxicity in the lesion affected area and a high intravascular stenosis inhibitory effect, can be provided with a specific crystal form of a water-insoluble drug when delivering medical device coated with a drug into the body.

The following crystal forms are preferably exemplified.

(1) Layer Including Crystalline Morphological Form of Long Hollow Object

The layer having a morphological form including crystals of a long hollow object is a drug coating layer in which a plurality of elongated bodies having long axes formed of crystals of the water-insoluble drug are present in a brush shape on the substrate surface. The plurality of elongated bodies are circumferentially arranged in a brush shape on the substrate surface. Each of the elongated bodies is independently present, has a length, and has one end (proximal) of the elongated body fixed to the substrate surface. The elongated bodies do not form a composite structure with adjacent elongated bodies, and are not connected to each other. The long axis of the crystal is nearly linear in shape. The elongated body forms a predetermined angle with respect to the substrate plane which the long axis intersects. The predetermined angle is in the range of 45° to 135°. The predetermined angle is preferably in the range of 70° to 110°, and more preferably in the range of 80° to 100°. It is more preferable that the long axis of the elongated body forms an angle of nearly 90° with respect to the substrate plane. At least near the distal, the elongated body is hollow. The cross section of the elongated body is hollow in a surface perpendicular to the long axis of the elongated body. The hollow cross section of the elongated body in a surface perpendicular to the long axis is a polygon. Examples of the polygon include a tetragon, a pentagon, and a hexagon. Accordingly, the elongated body has the distal (or distal surface) and the proximal (or proximal surface), and a side surface between the distal (or distal surface) and the proximal (or proximal surface) is formed as a long polyhedron which is constituted with a plurality of planes. The crystalline morphological form constitutes the whole of or at least a part of a plane on the substrate surface. For example, the layer including the crystalline morphological form of the long hollow object is a layer having the crystalline morphological form shown in SEM images of FIGS. 1 to 5.

For example, characteristics of the layer having the morphological form including the crystals of a long hollow object are as follows.

1) A plurality of elongated bodies (rod) having independent long axes, and the elongated body is hollow.

2) The elongated body has a rod shape.

3) The elongated bodies have long axes, and in many cases, is a polyhedron, in which the cross section of the elongated body in a surface perpendicular to the long axis is polygonal. Equal to or greater than 50% by volume of the elongated body crystal is a long polyhedron. The side surface of the polyhedron is mainly a tetrahedron. In some cases, the long polyhedron has a plurality of surfaces (grooves) which are formed of a reentrant angle in which a vertex is extended in a long axis direction. Herein, the reentrant angle means that at least one of the interior angles of the polygon of a cross section of the elongated body in a plane perpendicular to the long axis is greater than an angle of 180°.

4) In many cases, the elongated body having a long axis is a long polyhedron. When viewed in a cross section perpendicular to the long axis, the cross section is polygonal, and is observed as a tetragon, a pentagon, or a hexagon.

5) A plurality of elongated bodies having independent long axes stand in a row with an angle in a predetermined range, preferably in the range of 45° to 135° with respect to the substrate surface, that is, the plurality of elongated bodies having independent long axes nearly uniformly stand like a forest on the substrate surface. The region where the elongated bodies stand like a forest is nearly uniformly formed in the circumferential direction and the axial direction on the substrate surface. Each angle with respect to the substrate surface of each independent elongated body may be different or the same in the predetermined range.

6) One end (proximal) of each elongated body having an independent long axis is fixed to the substrate surface.

7) In some cases, in a portion near the substrate surface, particle-like, short rod-like or short curve-like crystals are laminated. The elongated body which directly or indirectly has a long axis on the substrate surface is present. Therefore, there is a case where the elongated bodies having long axes on the laminate stand like a forest.

8) A length in the axial direction of the elongated body having a long axis is preferably 5 μm to 20 μm, more preferably 9 μm to 11 μm, and still more preferably about 10 μm. A diameter of the elongated body having a long axis is preferably 0.01 μm to 5 μm, more preferably 0.05 μm to 4 μm, and still more preferably 0.1 μm to 3 μm.

9) Other morphological forms (for example, a plate shaped morphological form which is amorphous) are not mixed on the surface of the layer including the crystalline morphological form of a long hollow object, which is present in an amount equal to or greater than 50% by volume, and more preferably equal to or greater than 70% by volume, and is present as the crystalline morphological forms of 1) to 7). More preferably, almost all of the long hollow object is the crystalline morphological form of 7).

10) In the crystalline morphological form of the long hollow object, it is possible that other compounds are present in the drug coating layer including the water-insoluble drug constituting crystals. In this case, the compounds are present in a state of being distributed in the space between crystals (elongated body) of a plurality of the water-insoluble drugs which stand like a forest on a balloon substrate surface. In the ratio of the materials constituting the drug coating layer, the crystals of the water-insoluble drugs occupy a much greater volume than other compounds in this case.

11) In the crystalline morphological form of long hollow object, the water-insoluble drugs constituting crystals are present on the balloon substrate surface. In the drug coating layer of the balloon substrate surface having the water-insoluble drugs constituting crystals, a matrix by the excipient is not formed. Therefore, the water-insoluble drugs constituting crystals are not attached to the matrix material. The water-insoluble drugs constituting crystals are also not embedded in the matrix material.

12) In the crystalline morphological form of long hollow object, the drug coating layer may include crystal particles of the water-insoluble drugs which are arranged with regularity on the substrate surface, and excipient particles formed of an excipient which are irregularly arranged between the crystal particles. In this case, a molecular weight of the excipient is less than a molecular weight of the water-insoluble drugs. Therefore, the ratio that the excipient particles occupy per a predetermined area of the substrate is smaller than the ratio that crystal particles occupy and the excipient particles do not form a matrix. Here, the crystal particles of the water-insoluble drugs may be one of the elongated body, and since the excipient particles are present in a state of being much smaller than the crystal particles of the water-insoluble drugs, and are dispersed among the crystal particles of the water-insoluble drugs, there is a case where the excipient particles are not observed in the SEM image.

(2) Layer Including Flat Hair-Like Shape Crystalline Morphological Form

The flat hair-like shape crystalline morphological form to be described below occupies at least a part of the drug coating layer (including an amorphous form), equal to or greater than 50% by volume, equal to or greater than 80% by volume, (equal to or greater than 50% by volume as a crystal form, more and preferably equal to or greater than 70% by volume), and still more preferably nearly 100% by volume. In a case of occupying nearly 100% by volume, it is in a state that a plurality of crystalline morphological forms are not mixed, and only a single crystalline morphological form is present.

The layer including a flat hair-like shape crystalline morphological form is a drug coating layer in which crystals of a flatly elongated hair-like shape of crystals of the water-insoluble drug are randomly laminated on the substrate surface, and in which some of the crystals have a portion curved in shape, and crystals having other morphological forms are not mixed in the same crystal plane. In a case where an amorphous layer and a crystal layer are present, "not the same crystal plane" means that the amorphous film is present on the crystal layer. For example, the layer including the flat hair-like shape crystalline morphological form is a layer having the crystal form of Example 6 shown in FIG. 6A.

For example, characteristics of the layer including the flat hair-like shape crystalline morphological form are as follows.

1) A hair-like shape crystal having a long axis has a shape flatly jointed in a plurality of width directions, is not hollow, and has a tapered shape.

2) The joint shape of the hair-like shape crystal is randomly laminated on the substrate surface. The long axis is present in a state reclined along the substrate surface.

3) Some of the crystals have a portion curved in shape.

4) A length in the long-axis direction of the hair-like shape crystal is preferably 10 μm to 100 μm, more preferably about 20 μm, and is longer than a length of the crystalline morphological form of a long hollow object in many cases.

(3) Layer Including Morphological Form in which an Amorphous Film is Present on the Surface of the Flat Hair-Like Shape Crystal The layer is a drug coating layer in which the surface of the flat hair-like shape crystal is covered with an amorphous film. The layer including the morphological form in which an amorphous film is present on the surface of the flat hair-like shape crystal, in which a layer of an amorphous film is present on the flat hair-like shape crystal, is formed of two layers, one of the crystal and the other the amorphous film. For example, the layer including the morphological form in which an amorphous film is present on the surface of the flat hair-like shape crystal is a layer having the crystal form of Example 6 shown in FIG. 6B.

Specifically, on a certain plane (plane in which crystal/amorphous film are present), a certain crystal form is at least partly present, or a certain crystal form is present in an amount equal to or greater than 50% by volume, or equal to or greater than 80% by volume, (equal to or greater than 50% by volume as a crystal form, and more preferably equal to or greater than 70% by volume), still more preferably a plurality of crystal forms are not mixed, and an amorphous film may be present on the outside of a certain plane.

The crystal layers of the morphological form of the long hollow object, the morphological form of the flat hair-like shape, and the morphological form in which an amorphous film is present on the surface of the flat hair-like shape crystal have low toxicity and a high intravascular stenosis inhibitory effect when delivering medical device in which the substrate surface is coated with a drug into the body as a drug coating layer. While not limiting, it is considered that the reason is because solubility and retentivity in tissue after a drug having a certain crystal form is transferred into the tissue is affected. For example, in a case of an amorphous form, since solubility is high, even when the drug is transferred into a tissue, it immediately flows into the blood stream. Therefore, the retentivity in a tissue is low, and thus an excellent stenosis inhibitory effect cannot be obtained. On the other hand, the water-insoluble drug having the described specific crystal form effectively acts to inhibit the stenosis since when the drug is transferred into a tissue, one unit of the crystal becomes small, and therefore, the permeability into a tissue and the solubility thereof are excellent. In addition, it is considered that since the quantity of the drug remaining in a tissue as a large mass is small, the toxicity is low.

In particular, the layer including the crystalline morphological form of a long hollow object is a plurality of nearly uniform elongated bodies having long axes, and a morphological form which substantially uniformly stands in a row with regularity on the substrate surface. Therefore, the crystals transferred into a tissue have a small size (length in long-axis direction) of about 10 μm. For this reason, the drug uniformly acts on the lesion affected area, and tissue penetrability is increased. Further, it is considered that since the size of the crystals transferred is small, an excessive amount of the drug does not remain in the lesion affected area for an excessive amount of time, and the toxicity is not expressed, and a high stenosis inhibitory effect can be exhibited.

Water-Insoluble Drug

The water-insoluble drug means a drug that is insoluble or poorly soluble in water, and specifically, solubility in water is less than 5 mg/mL at pH 5 to 8. The solubility may be less than 1 mg/mL, and further, may be less than 0.1 mg/mL. The water-insoluble drug includes a fat-soluble drug.

Examples of some preferable water-insoluble drugs include immunosuppressive drugs such as cyclosporines including cyclosporine, immunoactive drugs such as rapamycin, anticancer drugs such as paclitaxel, an antiviral drug or an antibacterial drug, an antineoplastic tissue drug, an analgesic drug and an antiinflammatory drug, an antibiotic drug, an antiepileptic drug, an anxiolytic drug, an antiparalysis drug, an antagonist, a neuron blocking drug, an anticholinergic drug and a cholinergic drug, an antimuscarinic drug and a muscarinic drug, an antiadrenergic drug, an antiarrhythmic drug, an antihypertensive drug, a hormone drug, and a nutritional supplement.

The water-insoluble drug is preferably at least one selected from a group formed of rapamycin, paclitaxel, docetaxel, and everolimus. In the specification, rapamycin, paclitaxel, docetaxel, and everolimus include analogs and/or derivatives thereof as long as these have similar drug efficacy. For example, the paclitaxel is an analogue of the docetaxel. The rapamycin is an analogue of the everolimus. Among these, the paclitaxel is more preferable.

The water-insoluble drug may further include an excipient. The excipient is not limited as long as it is pharmaceutically acceptable, and examples thereof include water-soluble polymers, sugars, contrast agents, citric acid esters, amino acid esters, glycerol esters of short-chain monocarboxylic acid, pharmaceutically acceptable salts, surfactants, and the like. The ratio of the excipient and the water-insoluble drug is not limited, but specifically, the ratio excipient/water-insoluble drug is in the range from 0.5 to 4.0 (mol/mol), and more preferably, in the range from 1.0 to 3.2 (mol/mol). The excipient may be amino acid esters, preferably serine ethyl ester, and water-insoluble drug is paclitaxel.

Method for Preparing Crystalline Layer

A coating solution is prepared by dissolving a water-insoluble drug in a solvent. The coating solution is coated on a dilated balloon such that the solvent of the coating solution is slowly volatilized. Thereafter, the balloon is deflated after coating is dried, thereby preparing a drug coating layer including the crystal layer.

The solvent used is not particularly limited and is exemplified by tetrahydrofuran, ethanol, glycerin (also referred to as glycerol or propane-1,2,3-triol), acetone, methanol, dichloromethane, hexane, ethyl acetate, and water. Among these, a mixed solvent in which some from among tetrahydrofuran, ethanol, acetone, and water are mixed is preferable.

A coating solution is applied to the surface of a medical device (e.g. medical device, for example, balloon catheter, etc.) by using a coating apparatus. The coating apparatus includes a motor, a platform, and a dispensing tube. The motor is connected to a rotation member that is fixed to the proximal end of the medical device. The medical device is mounted on the rotation member and configured to rotate about its longitudinal axis. The medical device is supported on the platform so that the medical device is rotatable on the platform. The coating solution is coated on the surface of the medical device with the dispensing tube. The dispensing tube has a hollow tubular structure, and has an opening at the distal end. The lateral part of the distal portion of the dispensing tube is disposed to contact the surface of the medical device, and the coating solution is dispensed from the distal opening onto the surface of the medical device. The medical device is rotated about the longitudinal axis in the opposition direction (reverse direction) of dispensing the coating solution. The dispensing tube translates along the longitudinal axis of the medical device to apply the coating solution on the medical device. The coating solution applied on the surface of the medical device is dried to form a coating layer. The rotation of the medical device (balloon catheter) is made at 10-200 rpm, preferably 30-180 rpm, more preferably 50-150 rpm. The translational movement is made at 0.01-2 mm/sec, preferably 0.03-1.5 mm/sec, more preferably 0.05-1.0 mm/sec. The part of the medical device (balloon catheter) where a coating layer is formed has a round or annular shape in cross-section and its diameter is 1-10 mm, preferably 2-7 mm. The dispensing of the coating solution on the surface of the medical device is made at 0.01-1.5 μL/sec, preferably 0.01-1.0 μL/sec, more preferably 0.03-0.8 μL/sec.

Medical Device

The medical device can have the drug coating layer applied directly or through a pretreatment layer, such as a primer layer, on the surface of the substrate. The drug coating layer contains a drug at a density of 0.1 $\mu g/mm^2$ to 10 $\mu g/mm^2$, preferably at a density of 0.5 $\mu g/mm^2$ to 5 $\mu g/mm^2$, more preferably at a density of 0.5 $\mu g/mm^2$ to 3.5 $\mu g/mm^2$, even more preferably at a density of 1.0 $\mu g/mm^2$ to 3.0 $\mu g/mm^2$, but it is not particularly limited thereto.

The shape and materials of the substrate are not particularly limited. Metals and resins may be used as materials. The material may be any one of a film, a plate, a wire rod, and an irregularly shaped material, and may be a particulate.

The medical device used is not limited. Any medical device that is transplantable or insertable may be used. The medical device which is long, delivered in the non-dilated state with a reduced diameter in a body cavity such as blood, and enlarged in diameter in a circumferential direction at a part, such as a blood vessel or a tissue, to release a drug from the drug coating layer is preferable. Therefore, the medical device that is reduced in diameter to be delivered, and enlarged in diameter to be applied to an affected area is a medical device having a dilation portion. The drug coating layer is provided on at least a part of the surface of the dilation portion. That is, the drug is coated on, at least, the outer surface of the dilation portion.

The materials of the dilation portion of the medical device preferably have a certain degree of flexibility, and a certain degree of hardness such that the drug is released from the drug coating layer on the surface by being dilated when the medical device reaches a blood vessel or a tissue. Specifically, the medical device is constituted with a metal or a resin, and the surface of the dilation portion on which the drug coating layer is provided is preferably constituted of a resin. The resin constituting the surface of the dilation portion is not particularly limited, and preferable examples thereof include polyamides. That is, at least a part of the surface of the dilation portion of the medical device which is coated with a drug is a polyamide. Examples of the polyamide, which is not particularly limited as long as it is a polymer having an amide bond, include homopolymers such as polytetramethylene adipamide (Nylon 46), polycaprolactam (Nylon 6), polyhexamethylene adipamide (Nylon 66), polyhexamethylene sebacamide (Nylon 610), polyhexamethylene dodecamide (Nylon 612), polyundecanolactam (Nylon 11), polydodecanolactam (Nylon 12), coploymers such as a caprolactam/lauryl lactam copolymer (Nylon 6/12), a caprolactam/aminoundecanoic acid copolymer (Nylon 6/11), a caprolactam/co-aminononanoic acid copolymer (Nylon 6/9), a caprolactam/hexamethylene diammonium adipate copolymer (Nylon 6/66), and aromatic polyamides such as a copolymer of adipic acid and m-xylene diamine, or a copolymer of hexamethylene diamine and m,p-phthalic acid. Further, a polyamide elastomer which is a block copolymer in which Nylon 6, Nylon 66, Nylon 11, or Nylon 12 is a hard segment, and a polyalkylene glycol, a polyether, or an aliphatic polyester is a soft segment can be used as a substrate material for a medical device. The polyamides may be solely used, or two or more kinds thereof may be jointly used.

Specifically, as the medical device having the dilation portion, a long catheter having a dilation portion (stent) or a dilation portion (balloon) is exemplified (balloon catheter).

In the balloon of one embodiment, preferably, the drug coating layer is formed on the surface at the time of dilating, and the balloon is wrapped (folded), inserted into a blood vessel, a body cavity or the like, delivered to tissue or affected area, and enlarged in diameter in the affected area, and then, the drug is released.

Method of Treating Peripheral Artery Diseases in Lower Limbs

As mentioned above, a medical device is provided as DEB having an expandable member (e.g., a balloon) having a drug coating layer which has a crystalline morphological form including a plurality of crystal particles of water-insoluble drug regularly arranged and uniformly sized on the surface of the medical device. The medical device is inserted in peripheral blood vessels, through an incision of an access point made in an artery. An access point can be made in radial artery or femoral artery, which is called a trans-radial approach or a trans-femoral approach, respectively. The medical device is introduced in the artery through the access point using other medical devices like guidewires and guiding catheters to the lesion of peripheral artery diseases to be treated in the lower limbs. When the medical device is positioned next to the lesion, an expandable member is dilated by fluid and expanded. The drug coating layer of the surface of the expandable member contacts and is pressed to the wall of the blood vessels. The drug is immediately released from the surface of the expandable member, and at least part of a plurality of crystal particles are transferred to the vascular tissue of the blood vessels. The expandable member is deflated and the medical device is withdrawn from the blood vessels.

By using the medical device as described herein, methods are provided treating peripheral artery diseases in lower limbs. The lesions of peripheral artery diseases are formed by arterial sclerosis which is generated by/with aging, infection, diabetes mellitus, and the like in the blood vessels (arteries) of lower limbs. As described herein, it was shown that the size of the microparticulates generated in the lesion is small enough and generation of the relatively large microparticulates having a size that can cause embolization of peripheral blood vessels is suppressed. This is thought to be caused by crystal particles of paclitaxel uniformly arranged and constantly sized in the drug coating layer on the surface of the balloon. It was demonstrated that DEB as described herein is capable of reducing the risk of peripheral embolization because of less distribution of microparticulates in the muscle adjacent downstream peripheral blood vessels compared to DEB manufactured by others. This was shown in the experiments to see the effects of microparticulates on muscles adjacent downstream peripheral blood vessels using porcine lower limbs.

As described herein, a pharmacokinetic profile (PK profile) is provided by using DEB. This PK profile is achieved by uniform paclitaxel crystal particles in a micro size. A high drug concentration in tissue by day 7 after dilation of the balloon affects smooth muscle cell proliferation. After that, prompt clearance from the tissue does not inhibit endothelial cell growth. The DEB provides superior outcomes in both efficacy and safety. That is, the DEB disclosed herein can give no influence on the vascular remodeling, which reduces the risk of its late thrombosis. Although it strongly inhibits the stenosis, dual anti-platelet therapy (DAPT) expects to be limited for 4 weeks to the same extent that non-drug coated balloon provides. The PK profile comprises the area under the blood concentration-time curve (AUC) of the drug on day 0.04 (60 minutes) to day 7 after the balloon dilation is at least 200 ng day/mg tissue, the drug concentration in the tissue is 5 ng/mg tissue to 40 ng/mg, and more preferably 9 ng/mg tissue to 40 ng/mg tissue on day 7, the drug concentration in the tissue is 0.5 ng/mg tissue to 3 ng/mg tissue on day 28, and the reduction rate of the drug from 0.04 day to 1 day was at most 50%.

As described herein, it was shown that DEB provides uniform inhibitory effects of vascular intima thickening in the entire treated lesion (in the entire long lesion). The long lesion is treated by, for example, a balloon catheter having a longitudinal length in the range of 4 cm to 20 cm. This is achieved by the micro crystals of paclitaxel uniformly arranged and constantly sized in the drug coating layer on the surface of the balloon. Further, the micro crystals of paclitaxel are delivered without being detached from the surface of the balloon during a process to be delivered to the lesion of the treatment. DEB can be expanded in the lesion of the treatment while keeping the uniformity (regular arrangement and uniform sizing of a plurality of crystal particles) of the drug coating layer until dilated. This is how DEB can uniformly deliver drugs, such as paclitaxel to the entire lesion. The size of uniformly arranged paclitaxel crystals is not limited in particular. The crystal size can be, for example, both in the range from 0.5 μm to 5 μm, and in the range 5 μm to 30 μm.

EXAMPLES

Hereinafter, examples and the comparative examples will be described, but, the embodiments are not limited to the examples.

A. Manufacture or Preparation of Drug Eluting Balloon, or Preparation of Non-Drug Coated Balloon

Example 1

(1) Preparation of Coating Solution 1

L-serine ethyl ester hydrochloride (CAS No. 26348-61-8) (56 mg) and paclitaxel (CAS No. 33069-62-4) (134.4 mg) were weighed. Absolute ethanol (1.2 mL), tetrahydrofuran (1.6 mL), and RO (reverse osmosis) membrane-treated water (hereinafter, referred to as RO water) (0.4 mL) were respectively added thereto and dissolved, thereby preparing a coating solution 1.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 1 was coated on the dilated balloon such that the solvent of the coating solution is slowly volatilized to make the amount of paclitaxel be about 3 μg/mm$^2$. That is, a dispensing tube having an opening at the distal most end was transferred horizontally in the traverse direction and was placed on the surface of the balloon. At least a portion of the lateral side of the dispensing tube was contacted and disposed along the surface of the balloon. While at least a portion of the lateral side of the dispensing tube was maintained in contact with the surface of the balloon, the coating solution was dispensed from the opening at the distal most end of the dispensing tube. In this state the balloon was rotated about the longitudinal axis in the opposite direction (reverse direction) against the direction of the dispensing the coating solution from the distal opening. The translational movement of the dispensing tube along the longitudinal axis and the rotational movement of the balloon were adjusted, and concurrent with the beginning of the rotation, the coating solution was dispensed on the surface of the balloon at 0.053 μL/sec to perform coating of the balloon.

Thereafter, the coating was dried, thereby making a drug eluting balloon.

Example 2

(1) Preparation of Coating Solution 2

L-serine ethyl ester hydrochloride (70 mg) and paclitaxel (180 mg) were weighed. Absolute ethanol (1.5 mL), acetone (2.0 mL), tetrahydrofuran (0.5 mL), and RO water (1 mL) were added thereto respectively and dissolved, thereby preparing a coating solution 2.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 2 was coated on the dilated balloon such that the solvent of the coating solution is slowly volatilized to make the amount of paclitaxel be about 3 μg/mm$^2$.

That is, the coating was performed as in the Example 1 except that the coating solution was dispensed on the surface of the balloon at 0.088 μL/sec.

Thereafter, the coating was dried, thereby making a drug eluting balloon.

Example 3

(1) Preparation of Coating Solution 3

L-serine ethyl ester hydrochloride (70 mg) and paclitaxel (168 mg) were weighed. Absolute ethanol (1.5 mL), tetrahydrofuran (1.5 mL), and RO water (1 mL) were added thereto respectively and dissolved, thereby preparing a coating solution 3.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 3 was coated on the dilated balloon such that the solvent of the coating solution is slowly volatilized to make the amount of paclitaxel be about 3 μg/mm$^2$.

That is, the coating was performed as in the Example 1 except that the coating solution was dispensed on the surface of the balloon at 0.101 μL/sec.

Thereafter, the coating was dried, thereby making a drug eluting balloon.

Example 4

(1) Preparation of Coating Solution 4

L-serine ethyl ester hydrochloride (70 mg) and paclitaxel (180 mg) were weighed. Absolute ethanol (1.75 mL), tetrahydrofuran (1.5 mL), and RO water (0.75 mL) were added thereto respectively and dissolved, thereby preparing a coating solution 4.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 4 was coated on the dilated balloon such that the solvent of the coating solution is slowly volatilized to make the amount of paclitaxel be about 3 μg/mm$^2$.

That is, the coating was performed as in the Example 1 except that the coating solution was dispensed on the surface of the balloon at 0.092 μL/sec.

Thereafter, the coating was dried, thereby making a drug eluting balloon.

Example 5

(1) Preparation of Coating Solution 5

L-aspartic acid dimethyl ester hydrochloride (CAS No. 32213-95-9) (37.8 mg) and paclitaxel (81 mg) were weighed. Absolute ethanol (0.75 mL), tetrahydrofuran (0.96 mL), and RO water (0.27 mL) were added thereto respectively and dissolved, thereby preparing a coating solution 5.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 5 was coated on the dilated balloon such that the solvent of the coating solution is slowly volatilized to make the amount of paclitaxel be about 3 μg/mm$^2$.

That is, the coating was performed as in the Example 1 except that the coating solution was dispensed on the surface of the balloon at 0.055 μL/sec.

Thereafter, the coating was dried, thereby making a drug eluting balloon.

Example 6

(1) Preparation of Coating Solution 6

L-serine ethyl ester hydrochloride (56 mg) and paclitaxel (134.4 mg) were weighed. Absolute ethanol (0.4 mL), tetrahydrofuran (2.4 mL), and RO water (0.4 mL) were added thereto respectively and dissolved, thereby preparing a coating solution 6.

(2) Drug Coating on Balloon

A balloon catheter (manufactured by Terumo Corp., the material of the balloon (dilation portion) is a nylon elastomer) having a size of a diameter 3.0×a length 20 mm (dilation portion) when dilated was prepared. The coating solution 6 was coated on the dilated balloon such that the solvent of the coating solution is slowly volatilized to make the amount of paclitaxel be about 3 μg/mm$^2$.

That is, the coating was performed as in the Example 1 except that the coating solution was dispensed on the surface of the balloon at 0.053 μL/sec.

Thereafter, the coating was dried, thereby making a drug eluting balloon.

Comparative Example 1

IN.PACT® (manufactured by INVAtec JAPAN, Interventional Cardiology, 58(11), 2011, 1105-1109) which is a commercially available drug-eluting balloon catheter comprising paclitaxel and an excipient of urea was provided. The balloon in Comparative Example 1 is a drug eluting balloon of which the surface is coated with paclitaxel.

Comparative Example 2

A balloon catheter (manufactured by Terumo Corp., the material of the balloon (dilation portion) is a nylon elastomer) having a size of a diameter 3.0×a length 20 mm (dilation portion) when dilated was prepared. The balloon in Comparative example 2 is a non-drug coated balloon of which the surface is not coated with a drug.

B. Measurement of Amount of Paclitaxel Coated on Balloon

For the drug eluting balloon in Examples 1 to 6, the amount of paclitaxel coated on the balloon was measured according to the following procedure.

1. Method

After the prepared drug eluting balloon was immersed in a methanol solution, it was shaken with a shaking apparatus for 10 minutes, and then, paclitaxel coated on the balloon was extracted. The absorbance at 227 nm of the methanol solution by which paclitaxel was extracted was measured by high performance liquid chromatography using an ultraviolet-visible spectrophotometer, and the amount of paclitaxel per balloon ([μg/balloon]) was determined. In addition, the amount of paclitaxel per unit area of balloon ([$\mu g/mm^2$]) was calculated from the amount of obtained paclitaxel and the balloon surface area.

2. Result

Table 1 shows the obtained results. In addition, in Table 1, "Balloon surface area" represents a surface area (unit: $mm^2$) when the balloon is dilated, "per each balloon" in "Amount of PTX on a balloon" represents the amount of paclitaxel per one balloon (unit: μg/balloon), and "per unit area" in "Amount of PTX on a balloon" represents the amount of paclitaxel per surface area 1 $mm^2$ of the balloon (unit: $\mu g/mm^2$), respectively.

As shown in Table 1, the amount of paclitaxel coated on the balloon in all of Examples 1 to 6 is about 3 $\mu g/mm^2$, and it was possible to coat the target amount of paclitaxel on the balloon surface.

TABLE 1

| Examples | Coating solution No. | Amount of PTX on a balloon per each [μg/balloon] | Amount of PTX on a balloon per unit area [$\mu g/mm^2$] |
|---|---|---|---|
| 1 | Coating solution 1 | 588.9 | 3.1 |
| 2 | Coating solution 2 | 665.5 | 3.5 |
| 3 | Coating solution 3 | 652.6 | 3.5 |
| 4 | Coating solution 4 | 661.3 | 3.5 |
| 5 | Coating solution 5 | 653.3 | 3.5 |
| 6 | Coating solution 6 | 560.2 | 3.0 |

C. Observation of Drug Coating Layer of Drug Eluting Balloon by Scanning Electron Microscope (SEM)

1. Method

The drug eluting balloons in Examples 1 to 5 and Example 6 were dried, and after the dried drug eluting balloons were cut to an appropriate size, these were placed on a support, and platinum deposition was performed thereon. In addition, in the same manner, after a commercially available drug eluting balloon (IN.PACT) manufactured by INVAtec JAPAN in Comparative Example 1 also was cut to an appropriate size, it was placed on a support, and platinum deposition was performed thereon. The surface and the inside of the drug coating layers of these platinum deposited samples were observed by a scanning electron microscope (SEM).

2. Result

In the drug coating layers of the Examples, crystal layers having a morphological form of a long hollow object, a morphological form of a flat hair-like shape, and a morphological form in which an amorphous film is present on the surface of the flat hair-like shape crystals were observed.

SEM images shown in FIGS. 1 to 6 were obtained. FIGS. 1 to 5, which are SEM images of Examples 1 to 5, show a layer, including the morphological form of a long hollow object, and it was made clear that uniform paclitaxel crystals of the long hollow objects having a length of about 10 μm are uniformly formed on the balloon surface. These paclitaxel crystals of the long hollow objects have long axes, and the elongated bodies (about 10 μm) having the long axes were formed so as to be in a direction nearly perpendicular to the balloon surface. The diameter of an elongated body was about 2 μm. In addition, the cross section of the elongated body in a surface perpendicular to the long axis was a polygon. The polygon was, for example, a polygon of a tetragon. Further, these nearly uniform long hollow objects of paclitaxel were uniformly and densely (at the same density) formed on the entire surface of the balloon in the same morphological form (structure and shape).

Figure 6A:
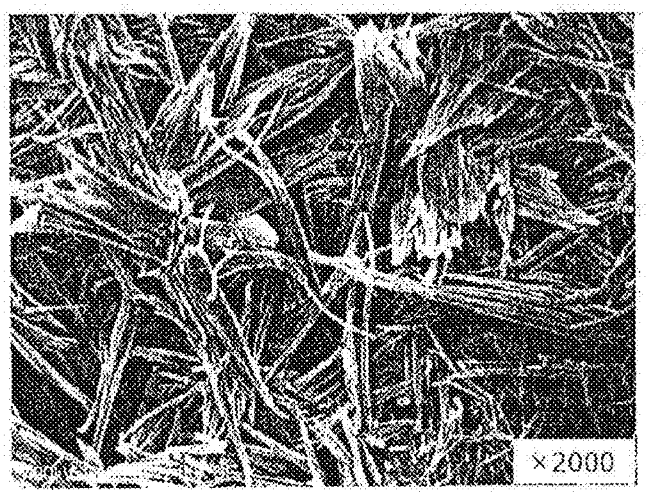
FIG. 6A is a diagram showing a SEM image at 2,000 times magnification of crystals observed on the substrate surface of the drug coating layer prepared in Example 6.
Figure 6B:
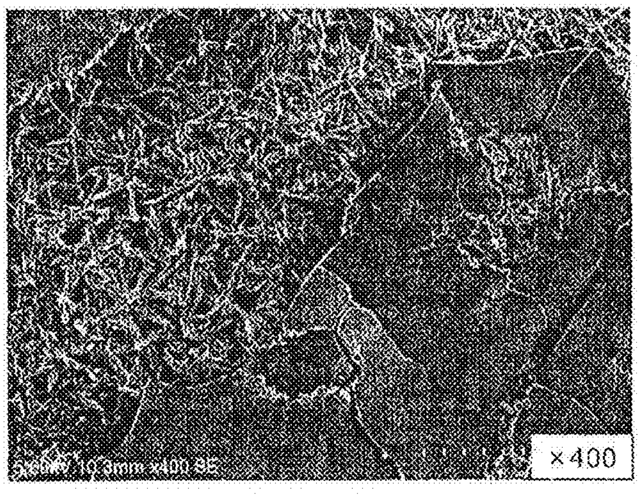
FIG. 6B is a diagram showing a SEM image at 400 times magnification of crystals observed on another portion of the substrate surface of the drug coating layer prepared in Example 6.

On the other hand, SEM images of FIG. 6A and FIG. 6B in Example 6 show a layer including a morphological form of a flat hair-like shape and a morphological form in which an amorphous film is present on the surface of the flat hair-like shape crystals, which were paclitaxel crystals of a flatly elongated hair-like shape. Many of these crystals have a comparatively large size equal to or greater than 20 μm, and the long axes are present in a state reclined along the balloon surface (FIG. 6A). Further, as shown in FIG. 6B, a region in which the upper portion of a layer including a morphological form of a flat hair-like shape is covered with an amorphous film was present. In the region, the layer including a morphological form in which a layer of an amorphous film is present on the flat crystal structure, two layers are formed of the crystals and the amorphous film, and the amorphous film is present on the surface of the flat hair-like shape crystals.

Figure 7:
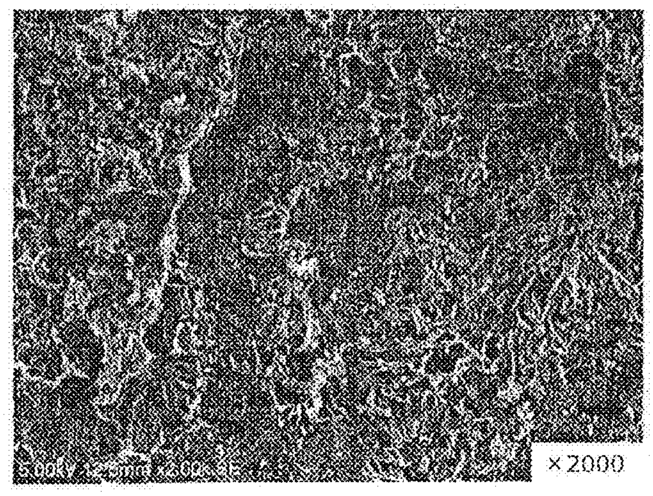
FIG. 7 is a diagram showing a SEM image at 2,000 times magnification of crystals observed on the substrate surface of the drug coating layer of a commercially available drug eluting balloon (IN.PACT) manufactured by INVAtec JAPAN in Comparative Example 1.

FIG. 7 in Comparative example 1 is a SEM image of the drug coating layer of a commercially available drug eluting balloon (IN.PACT) manufactured by INVAtec JAPAN. In this, amorphous material and crystals were mixed in the same plane. It was observed that most of them were nearly amorphous, and needle-like crystals were partly mixed in the same plane.

D. Intravascular Stenosis Inhibitory Effect in a Pig Coronary Artery and Effect on Blood Vessel Remodeling For Examples 1 and 6, Comparative Example 1 (C1: commercially available balloon), and Comparative Example 2 (C2: non-drug coated balloon), the intravascular stenosis inhibitory effect in a pig coronary artery and an effect on blood vessel remodeling were evaluated in according to the following procedure.

1. Method (1) A guiding catheter with a guide wire was inserted by an 8 Fr sheath, and guided to the left and right coronary artery opening portion under X-ray fluoroscopy.

(2) Angiography of each coronary artery was performed (coronary artery: left anterior descending coronary artery (LAD), right coronary artery (RCA), and left circumflex coronary artery (LCX)), and a diameter of coronary artery obtained by angiography was measured by a QCA software.

(3) A site in which a diameter of a stent is 1.2 times, and a diameter of the drug eluting balloon is 1.3 times with respect to a diameter of a blood vessel was selected, and work after stent placement was performed.

(4) After extended for 30 seconds such that BMS (bare metal stent) stent (stent diameter 3 mm×length 15 mm) in the coronary artery selected is 1.2 times, a balloon catheter for the stent placement was removed. At the stent placement site, after the drug eluting balloon (balloon diameter 3 mm×length 20 mm) having the drug coating layer prepared in Examples 1 and 6 and Comparative Examples 1 and 2 was dilated for 1 minute so as to be 1.3 times with respect to the diameter of a blood vessel, the balloon catheter was removed.

(5) After the drug eluting balloon was dilated, the guiding catheter and the sheath were removed. After a central side of a carotid artery was ligated, a gap of muscles of an incision opening of cervical region was sutured with a suture, and the skin was sutured by a surgical stapler for sutures.

(6) 28 days after the balloon dilatation, autopsy was performed.

Calculation Method of Intravascular Stenosis Rate

An intravascular stenosis rate was calculated in according to the following procedure.

Blood vessel images were taken by a Leica microscope and a pathology imaging system. By these images, internal area of an external elastic lamina area, internal elastic lamina area, internal area of lumen, internal area of stent were measured.

Area stenosis rate (%) was calculated from "area stenosis rate=(neointimal area/internal elastic lamina area)×100".

Calculation Method of Fibrin Content, Fibrin Content Score

Evaluation of fibrin content was performed in all circumferences of blood vessel according to the method of Suzuki et al. (Suzuki Y., et. al Stent-based delivery of sirolimus reduces neointimal formation in aprocine coronary model. Circulation 2001; 1188-93).

The content of the score of fibrin content is as follows.

Score 1: Fibrin localized in a blood vessel was observed, or fibrin is moderately deposited in a region less than 25% of all circumferences of blood vessel observable near a strut of the stent.

Score 2: Fibrin is moderately deposited in a region greater than 25% of all circumferences of blood vessel observable, or fibrin is heavily deposited in a region less than 25% of all circumferences of blood vessel observable between the struts and the proximity of the strut.

Score 3: Fibrin is severely deposited in a region greater than 25% of all circumferences of blood vessel observable.

In addition, all the scores were obtained by calculating the average value of the three locations, that is, a proximal location, a middle location, and a distal location of the stent placement sites for each blood vessel.

Endothelialization Score Calculation Method, Endothelialization Score

The content of an endothelialization score is as follows.

Score 1: Up to 25% of all circumferences of vascular lumen observable is covered with endothelial cells.

Score 2: 25% to 75% of all circumferences of vascular lumen observable is covered with endothelial cells.

Score 3: Equal to or greater than 75% of all circumferences of vascular lumen observable is covered with endothelial cells.

In addition, all the scores were calculated as an average value of three locations, that is, a proximal, a middle and a distal location to the stent placement site, for each blood vessel.

2. Results for Intravascular Stenosis Inhibitory Effect in a Pig Coronary Artery An intravascular stenosis rate was calculated according to the above-described procedure. Table 2 shows the obtained results. In Table 2, 1 and 6 in a column of Examples/Comparative Examples are Examples, and C1 to C2 are Comparative Examples.

Figure 8:
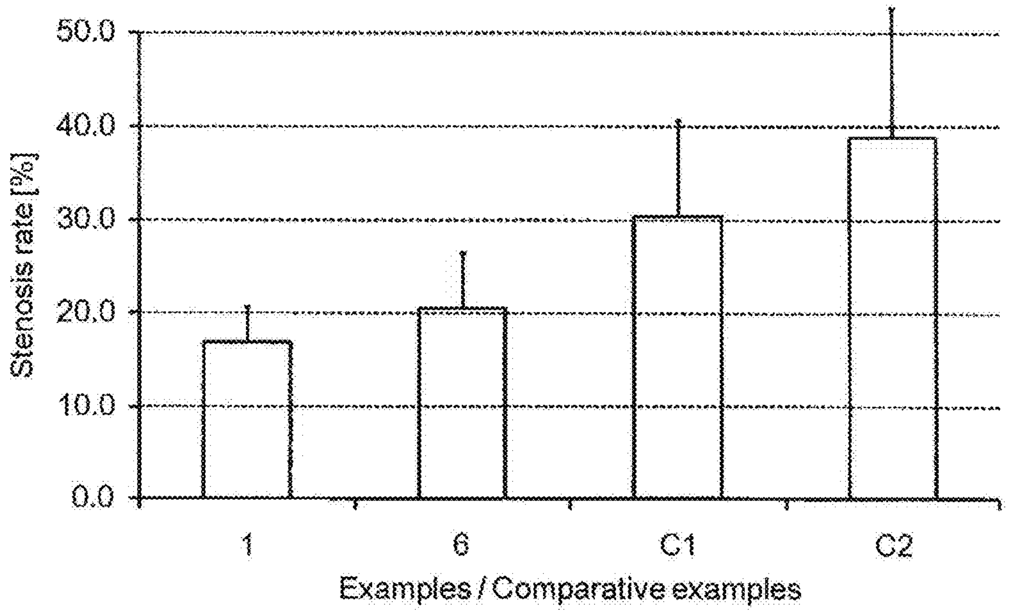
FIG. 8 is a graph of an intravascular stenosis rate (%) showing an inhibitory effect on an intravascular stenosis in a pig coronary artery.

In addition, FIG. 8 is a graph showing the blood vessel stenosis rate of Examples 1 and 6, and of Comparative Examples C1 to C2 for the intravascular stenosis inhibitory effect in pig coronary arteries. In FIG. 8, the horizontal axis represents Examples or Comparative Examples, the numbers 1 and 6 mean Examples 1 and 6, respectively, and the numbers with letters, that is, C1 to C2 mean Comparative Example 1 (C1) and Comparative Example 2 (C2), respectively. In addition, the vertical axis represents the area stenosis rate (unit: %) of a blood vessel.

In Comparative Example 2 (C2), the area stenosis rate of a blood vessel treated with the non-drug coated balloon as a non-drug treated control was 38.9%. The area stenosis rate of a blood vessel treated with the drug eluting balloon in Example 6 was 20.6%, and a significant stenosis inhibitory effect was confirmed as compared to the non-drug treated control. On the other hand, the area stenosis rate of a blood vessel treated with the commercially available drug eluting balloon (IN.PACT) in Comparative Example 1 was 30.4%, and it was found that the area stenosis rate tends to be decreased as compared to the non-drug coated balloon; however, it was estimated that there is sufficient room for improvement in the effect.

In contrast, the area stenosis rate of a blood vessel treated with the drug eluting balloon according to Example 1 was 16.8%, and a significant stenosis inhibitory effect was observed as compared to the non-drug treated control and the IN.PACT of Comparative Example 1 (C1). In addition, it showed a stronger effect than in Example 6, and the most excellent stenosis inhibitory effect was obtained.

Based on what has been described above, it was made clear that the drug eluting balloon of the drug coating layer having the paclitaxel crystalline morphological form according to Examples 1 and 6 exhibits a significantly stronger stenosis inhibitory effect than the commercially available drug eluting balloon.

TABLE 2

| Examples/ Comparative Examples | Stenosis rate [%] | S.D. |
|---|---|---|
| 1 | 16.8 | 3.9 |
| 6 | 20.6 | 5.9 |
| C1 | 30.4 | 10.3 |
| C2 | 38.9 | 13.8 |

3. Results for Blood Vessel Remodeling after Stent Placement in a Pig Coronary Artery (Toxicity)

As the effect (toxicity) on the blood vessel remodeling after the stent placement in a pig coronary artery, the fibrin content score and endothelialization score were observed. The results are shown in Table 3. Moreover, the larger the number the fibrin content score is, the larger the fibrin content is, which is not preferable. On the other hand, the smaller the number the endothelialization score is, the less blood vessel is covered with the endothelial cells, which is not preferable. In Table 3, 1 and 6 in a column of Examples/Comparative Examples are Examples, and C1 and C2 are Comparative Examples.

The fibrin content score and endothelialization score of a blood vessel treated with the non-drug coated balloon as a non-drug treated control in Comparative Example 2 (C2) do not have an influence on the vascular remodeling since there is no effect (toxicity) by drugs, and the scores were 1.00±0.00 and 3.00±0.00, respectively.

The fibrin content score and endothelialization score in Comparative Example 1 (C1) were 1.27±0.15 and 2.80±0.11, respectively, and the scores were nearly the same as those in the non-drug coated balloon. It is estimated that effect (toxicity) on the vascular remodeling is also small since the stenosis inhibition effect by drugs is small.

On the other hand, the fibrin content score and endothelialization score of a blood vessel treated with the drug eluting balloon according to Example 6 were 2.61±0.16 and 1.78±0.17, respectively, and it was suggested that the effect on the vascular remodeling was great as compared to those of Comparative Example 1 (C1) and Comparative Example 2 (C2). It is considered that this is because the stenosis inhibition effect is stronger than in Comparative Example 1 (C1) and Comparative Example 2 (C2).

In contrast, the fibrin content score and endothelialization score of a blood vessel treated with the drug eluting balloon according to Example 1 were 1.53±0.17 and 2.87±0.09, respectively, and it was made clear that the effect (toxicity) on the vascular remodeling was the same as that of the commercially available product in Comparative Example 1 (C1), and in spite that high stenosis inhibition effect was obtained, the toxicity was extremely low.

Based on what has been described above, the drug eluting balloon of the drug coating layer having the paclitaxel crystalline morphological form according to Example 6 has a significantly stronger stenosis inhibition effect. Further, it was made clear that the drug eluting balloon of the drug coating layer having the paclitaxel crystalline morphological form according to Example 1 has a significantly stronger stenosis inhibition effect, hardly exhibits the effect (toxicity) on the vascular remodeling, and thus, it is an excellent drug eluting balloon in terms of effectiveness and side effects (toxicity).

TABLE 3

| Examples/ Comparative Examples | Fibrin content score | Endothelialization score |
|---|---|---|
| 1 | 1.53 ± 0.17 | 2.87 ± 0.09 |
| 6 | 2.61 ± 0.16 | 1.78 ± 0.17 |
| C1 | 1.27 ± 0.15 | 2.80 ± 0.11 |
| C2 | 1.00 ± 0.00 | 3.00 ± 0.00 |

E. Particulate Sizes Generated from the Drug Eluting Balloon

For the drug eluting balloon in Example 7 and Comparative Example 3 (C3), particulate suspensions were generated by tracking drug eluting balloon through a simulated peripheral model and collected.

Example 7

Preparation of Drug Eluting Balloon

A balloon catheter (manufactured by Terumo Corp., the material of the balloon (dilation portion) is a nylon elastomer) having a size of a diameter 7.0×a length 200 mm (dilation portion) when dilated was prepared.

Coating solution 2 was prepared. The coating solution 2 was coated on the dilated balloon such that the solvent of the coating solution is slowly volatilized to make the amount of paclitaxel be about 3 $\mu g/mm^2$.

That is, the coating was performed as in the Example 2.

Comparative Example 3

IN.PACT® (manufactured by INVAtec/Medtronic, Inc., same as mentioned in Comparative Example 1 above) which is a commercially available balloon catheter having a size of a diameter 7.0×a length 120 mm (dilation portion) when dilated was provided. The balloon in Comparative Example 3 is a drug eluting balloon of which the surface is coated with paclitaxel.

1. Method

Particulate suspensions were generated according to the following procedure. A guiding sheath was filled with normal saline and was set having an angle of about 45 degrees. And then, a guide wire was passed through a lumen of the guiding sheath. During this test, normal saline in the guiding sheath was kept at 37° C. The drug eluting balloon was tracked over a guide wire for 1 minute until the balloon exited the model (the guiding sheath) into a mock vessel made of silicone rubber tubing in which the guiding sheath is placed. The balloon was inflated to 11 atm, held for 1 minute, deflated, and retracted through the model. A guiding sheath was flushed with physiological salt solution. The mock vessel was flushed with normal saline. All flush solutions were pooled in glass vials. Measurement of particulate counts and sizes were performed by a Liquid Particle Counter HIAC 8000A (Hach Company) and a microscope VH-5500 (KEYENCE).

2. Result

Figure 9A:
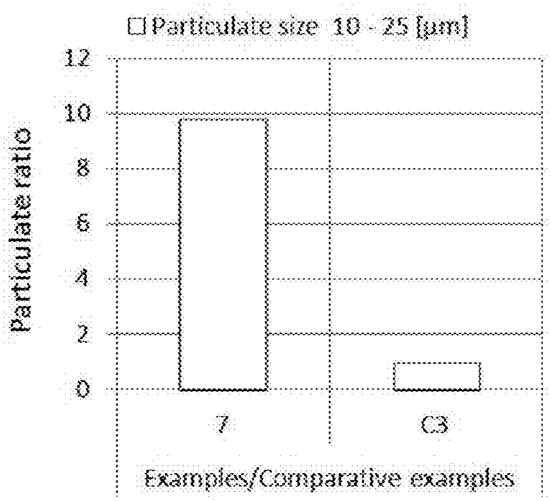
FIGS. 9A and 9B are graphs showing the particulate ratios of particle size 10-25 μm and 100-900 μm, respectively, of Example 7 and Comparative Example 3.
Figure 9B:
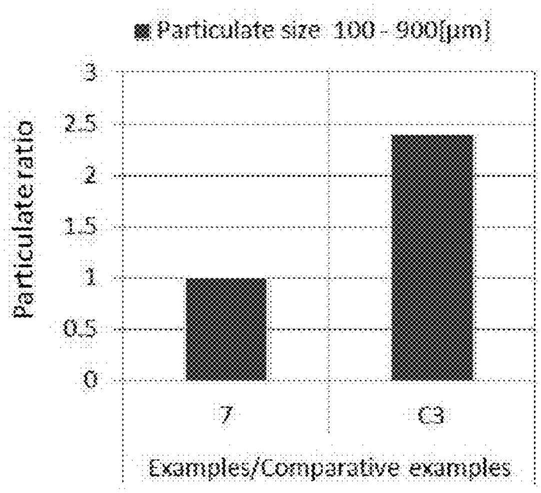

Particulates generated by the drug eluting balloon tracked through a simulated peripheral model with balloon expansion in a silicone rubber mock vessel (mean total counts per balloon catheter) was measured. The results are shown in FIG. 9A and FIG. 9B. In FIG. 9A and FIG. 9B, 7 is Example, and C3 is Comparative Example 3.

It was shown that the drug eluting balloon in Example 7 generated an approximate 10-fold higher number of particulates having a diameter of 10-25 μm (fine particulates) per balloon catheter than the drug eluting balloon (IN.PACT®) in Comparative Example C3. In addition, the drug eluting balloon in Example 7 also generated fewer large-sized particulates 100-900 μm than IN.PACT in Comparative Example C3. In this embodiment, greater than 90% of the total particulates generated from the drug eluting balloon in Example 7 was 10-25 μm in diameter, and the rest (10% or less) of the particulates is 100-900 μm in diameter as shown in FIG. 9A and FIG. 9B.

F. Histologic Evaluation Downstream Vascular and Skeletal Muscle

For the drug eluting balloon in Example 7 and Comparative Example 4 (C4), histologic evaluation of downstream vascular and skeletal muscle (in the peripheral arteries of the lower limb) was performed in according to the following procedure.

Comparative Example 4 (C4)

Comparative Example 4 (C4) in Table 4 is data of the commercially available drug coating balloon (Lutonix®) manufactured by Bard, that is referred to the literature (Catheterization and Cardiovascular Interventions 83, 2014, 132-140), which comprises paclitaxel and a carrier comprised of polysorbate and sorbitol.

1. Method

Particulate suspensions were generated by using a simulated peripheral model as in Example 7. Five porcine were designated to histologic evaluation of downstream vascular and skeletal muscle. After the drug eluting balloon treatment procedure has concluded, the animals were recovered and allowed to reach the predetermined 29±1 day survival time point. A single animal received intra-arterial injection of either 1× clinical dose (3 μg/$mm^2$ paclitaxel) or 3× dose (correspond to 9 μg/$mm^2$ paclitaxel) particulate suspension or control suspension to the left and right iliofemoral arteries. For each injection, the guiding catheter was positioned in a distal end of bifurcation of superficial femoral arteries and deep femoral arteries and paclitaxel particle suspension or control suspension was injected over a period of approximately 5 sec. Immediately following injection, the catheter was flashed with approximately 20 ml of normal saline to ensure the entire suspension had been delivered to the target area. An angiogram was performed to assess vessel patency. The presence of emboli within lower limb muscles was evaluated at 29±1 day by sectioning the semitendinosus, semimembranous, biceps femoris, Gastroconnemius femoris, musculus soleus, flexor digitorum profundus and flexor digitorum superficialis with parallel cuts at 1-2 cm apart. Histologic sections were prepared on a microtome at 3-4 microns and stained with hematoxylin and eosin (H&E). The histologic sections immunostained with anti-von Willebrand factor antibodies (Abcam) to detect endothelial cells. Histologic sections were examined to identify and quantify any embolic particulate as well as any associated regions of ischemic necrosis/inflammation. The number of arterioles with findings was expressed as a percentage of total number of arterioles histologic section.

Histological analyses of downstream skeletal muscle were performed to determine whether there is any evidence of ischemia from downstream emboli.

2. Result

Percentage of arterioles with any pathological findings downstream such as emboli and necrosis were evaluated. Table 4 shows the obtained results. In Table 4, "7" in column of Examples/Comparative Examples is an Example, and "C4" is a Comparative Example.

In Example 7, the percentage of arterioles with any pathological findings downstream of 3× dose treated arteries was maximally 0.012% at 28 days. It was showed that changes in skeletal muscle sections were overall very low. In addition, the percentage of downstream emboli and/or necrosis observed in Example 7 was less than Lutonix® according to Comparative Example 4 (C4) (Catheterization and Cardiovascular Interventions, 83, 2014, 132-140). Example 7 showed favorable downstream safety. It was shown that the drug eluting balloon as described herein has an effect with the decreased level of necrosis in the peripheral arteries.

TABLE 4

| Examples/ Comparative Examples | PTX dose [μg] | Thromboemboli/Vasculitis (arterioles with findings/total) [%] |
|---|---|---|
| 7 | 15825.6 (×1 dose) | 0.002 |
| 7 | 47476.8 (×3 dose) | 0.012 |
| C4 | 3014.4 | 0.18 |
| C4 | 12057.6 | 0.24 |

G. Drug Concentration in Downstream Muscle

For the drug eluting balloon in Example 8 and Comparative Example 5 (C5), a concentration of paclitaxel distributed in downstream muscle was evaluated in according to the following procedure.

Example 8

Preparation of Drug Eluting Balloon

A balloon catheter (manufactured by Terumo Corp., the material of the balloon (dilation portion) is a nylon elastomer) having a size of a diameter 6.0×a length 40 mm (dilation portion) when dilated was prepared.

Coating solution 2 was prepared. The coating solution 2 was coated on the dilated balloon such that the solvent of the coating solution is slowly volatilized to make the amount of paclitaxel be about 3 μg/$mm^2$.

That is, the coating was performed as in the Example 2.

Comparative Example 5 (C5)

"C5" in Table 5 is from the data of IN.PACT® normalized to the dose of Example 8. The IN.PACT® data was presented by R. J. Melder, Sc. D. at LINC 2013 (IN.PACT DEB technology and Pre-clinical Science).

1. Method

Three porcine animals were designated to evaluate the amount of paclitaxel distributed in downstream muscle (in the peripheral arteries of the lower limb). At the treatment procedure, angiography was utilized to identify target treatment sites within the iliofemoral and superficial femoral arteries. One drug eluting balloon treatment was performed per animal. After the drug eluting balloon treatment procedure has concluded, the animals were recovered and allowed to reach the predetermined 1 day (24±0.5 hours) survival time point. Muscles (beneath dilated segment [treatment site] and downstream) was carefully dissected from surrounding tissue at 1 day (24±0.5 hours) following treatment with the drug eluting balloon. The paclitaxel concentration measurement in muscle was performed by LC-MS/MS analysis.

2. Result

The amount of paclitaxel distributed in downstream muscle correlates with sequence of drug exposure was evaluated. Table 5 shows the paclitaxel concentration in downstream muscle. In Table 5, "8" in column of Examples/Comparative Examples is an Example, and "C5" is a Comparative Example.

The paclitaxel concentration in downstream muscle observed in Example 8 is less than IN.PACT of Comparative Example 5 (C5).

Based on what has been described above, it was made clear that the drug eluting balloon disclosed herein is capable of reducing the risk of peripheral embolization because of less distribution of (large-sized) micro-particulates in downstream muscle compared to drug eluting balloon manufactured by others.

TABLE 5

| Examples/ Comparative Example | PTX concentration in downstream Muscle [ng/mg] |
|---|---|
| 8 | 0.0176 |
| C5 | 0.0529 |

H. Pharmacokinetics in Porcine Ilio-Femoral Arteries

For the drug eluting balloon in Example 9 and Comparative Example 6-a (C6-a) to Comparative Example 8-a (C8-a), Comparative Example 9 (C9), pharmacokinetics in porcine ilio-femoral arteries was evaluated in according to the following procedure.

Example 9

Preparation of Drug Eluting Balloon

A balloon catheter (manufactured by Terumo Corp., the material of the balloon (dilation portion) is a nylon elastomer) having a size of a diameter 6.0×a length 40 mm (dilation portion) when dilated was prepared.

Coating solution 2 was prepared. The coating solution 2 was coated on the dilated balloon such that the solvent of the coating solution is slowly volatilized to make the amount of paclitaxel be about 3 μg/$mm^2$.

That is, the coating was performed as in the Example 2.

Comparative Example 6-a (C6-a)

Figure 10:
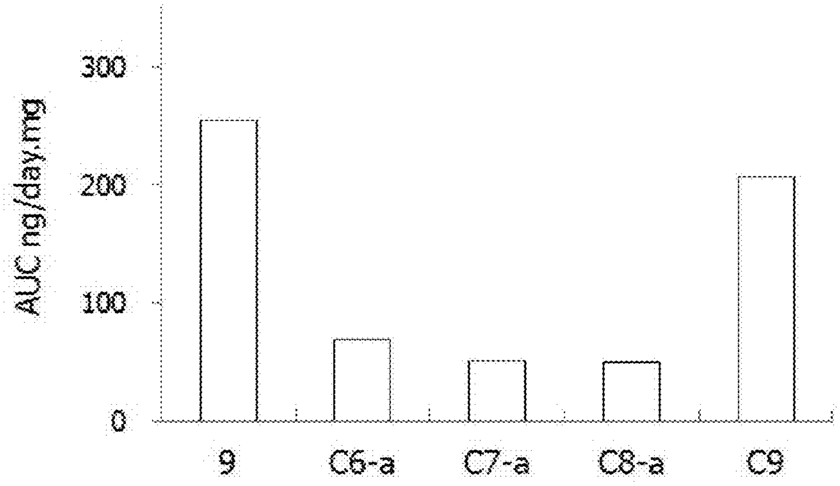
FIG. 10 is a graph showing the AUC of the drug on 0.02-0.04 day (0.5-1 hour) to 7 day of Example 9 and of Comparative Examples C6 to C9 for the transfer in the porcine femoral arterial tissue.
Figure 11:
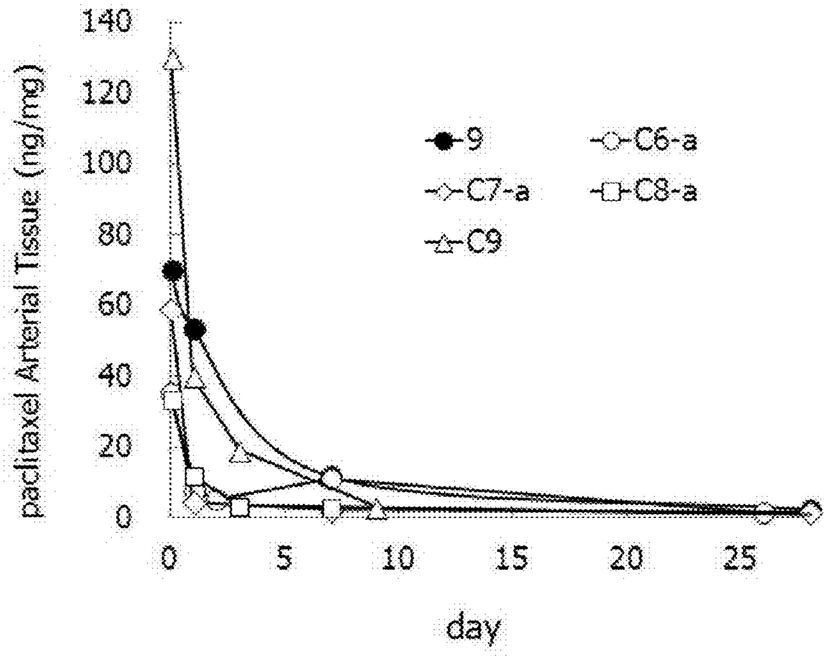
FIG. 11 is a graph showing the pharmacokinetic profile up to 27±1 day of Example 9 and of Comparative Examples C6 to C9 for the transfer in the porcine femoral arterial tissue.

Comparative Example 6-a (C6-a) in FIG. 10 and FIG. 11 is from the data of IN.PACT®. The IN.PACT® data was presented by R. J. Melder, Sc. D. at LINC 2013 (IN.PACT DEB technology and Pre-clinical Science).

Comparative Example 7-a (C7-a)

Comparative Example 7-a (C7-a) in FIG. 10 and FIG. 11 is from the data of Lutonix®. The Lutonix® data was presented by R. Virmani, MD at LINC 2014 (Pre-clinical safety data and technology review).

Comparative Example 8-a (C8-a)

Comparative Example 8-a (C8-a) in FIG. 10 and FIG. 11 is from the data of Cotavance®. The Cotavance® data was referred to in the literature (Cardiovascular Interventions, 6, 8, 2013, 883-890) and was presented by R. Virmani, MD (Pros and Cons of Different Technologies in Peripheral Arteries: Insights from A Pathologist).

Comparative Example 9 (C9)

Comparative Example 9 (C9) in FIG. 10 and FIG. 11 is from the data of Freeway®. The Freeway® data was presented by R. P. Strandmann at euro PCR 2013 (Effect of drug-coated balloon on porcine peripheral arteries: physiologic vascular function, safety and efficacy experiments).

1. Method

Twenty-four porcine animals were designated to pharmacokinetic study. At the treatment procedure, angiography was utilized to identify target treatment sits within the iliofemoral and superficial femoral arteries In the studies, two arteries (left and right iliofemoral arteries) were used in each animal. Angiography was performed prior, during and post-treatment to evaluate treatment and blood flow. After the drug eluting balloon treatment procedure has concluded, the animals were recovered and allowed to reach the predetermined 1-hr and 1, 7, and 28 days survival time point. A carotid artery cut down was performed and a sheath was placed for vascular access. The target tissue was carefully dissected from surrounding tissue at 1-hr and at 1, 7, and 28 days following treatment with the drug eluting balloon. The paclitaxel concentration measurement in tissue was performed by LC-MS/MS analysis.

2. Result

Pharmacokinetics in porcine femoral arteries was evaluated. FIG. 10 is a graph showing the AUC (area under the curve) of the drug on 0.02-0.04 day (0.5-1 hour) to 7 day of Example 9 and of Comparative Examples C6 to C9 for the transfer in the porcine femoral arterial tissue. In FIG. 10, the horizontal axis represents Example or Comparative Examples, the number “9” means Example 9, and the numbers with letters, that is, “C6-a” to “C9” mean Comparative Example 6-a (C6-a), Comparative Example 7-a (C7-a), Comparative Example 8-a (C8-a) and Comparative Example 9 (C9). In addition, the vertical axis represents the AUC (ng·day/mg) of drug on 0.04 day to 7 day in the target arterial tissue.

The AUC of the drug on 0.04 day (1 hour) to 7 day in the target arterial tissue after the balloon dilation observed in Example 9 was 254 ng·day/mg, which is higher than Comparative Example 6-a (C6-a), Comparative Example 7-a (C7-a), Comparative Example 8-a (C8-a) and Comparative Example 9 (C9). In addition, FIG. 11 is a graph showing the pharmacokinetic profile up to 27±1 day of Example 9 and of Comparative Examples C6 to C9 for the transfer in the porcine femoral arterial tissue. In FIG. 11, 9 is an Example and C6 to C9 are Comparative Examples. The horizontal axis represents day(s) after dilation of the drug eluting balloon. In addition, the vertical axis represents drug concentration in the target arterial tissue.

The AUC of the drug on 0.04 day to 7 day obtained in Example 9 was the highest compared to drug eluting balloons manufactured by others, which was referred to the literature, and the reduction rate of drug from 0.04 day (1 hour) to 1 day was at most 50%. After 7 day, the drug concentration in the tissue decreased to 2 ng/mg tissue by the 28 day.

The pharmacokinetic profile observed in Example 9 showed a high drug concentration in the tissue by 7 day after dilation of the balloon, and after that, it promptly cleared and maintained low concentration by day 28. A high drug concentration in the tissue by 7 day affects smooth muscle cell proliferation, after that prompt clearance from the tissue does not inhibit endothelial cell growth. So, drug eluting balloon as described herein provides superior outcomes in both efficacy and safety.

I. Intravascular Stenosis Inhibitory Effect in a Porcine Coronary Artery

For the drug eluting balloon in Example 10 and Comparative Example 6-b (C6-b) to Comparative Example 8-b (C8-b), Comparative Example 10 (C10) to Comparative Example 11 (C11), intravascular stenosis inhibitory effect in a porcine coronary artery was evaluated in according to the following procedure.

Example 10

Preparation of Drug Eluting Balloon

A balloon catheter (manufactured by Terumo Corp., the material of the balloon (dilation portion) is a nylon elastomer) having a size of a diameter 3.0×a length 20 mm (dilation portion) when dilated was prepared. Coating solution 2 was prepared. The coating solution 2 was coated on the dilated balloon such that the solvent of the coating solution is slowly volatilized to make the amount of paclitaxel be about 3 μg/mm$^2$.

That is, the coating was performed as in the Example 2.

Comparative Examples 6-b (C6-b)

Figure 12:
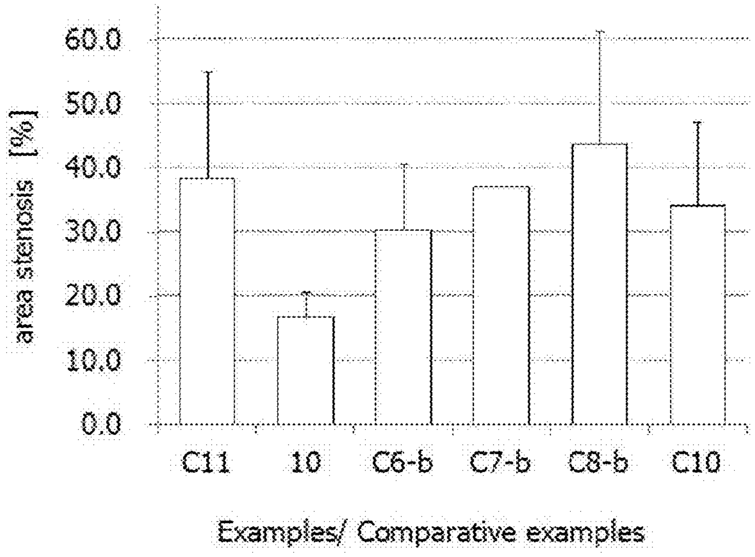
FIG. 12 is a graph showing percent area stenosis at 28 days of Example 10 and of Comparative Examples C6-b to C8-b, C10 and C11 for the intravascular stenosis inhibitory effect in porcine coronary arteries.

As drug eluting balloon of Comparative Example 6-b (C6-b) in FIG. 12, IN.PACT® (manufactured by INVAtec/Medtronic, Inc.) was provided. The balloon catheter having a size of a diameter 3.0×a length 20 mm (dilation portion) when dilated was prepared.

Comparative Example 7-b (C7-b)

Comparative Example 7-b (C7-b) in FIG. 12 is from the data of Lutonix®. The Lutonix® data was presented by R. Virmani, MD (Pros and Cons of Different Technologies in Peripheral Arteries: Insights from A Pathologist).

Comparative Example 8-b (C8-b)

Comparative Example 8-b (C8-b) in FIG. 12 is from the data of SeQuent Please). The SeQuent® data was referred to in the literature (Thrombosis and Haemostasis, 105, 5, 2011, 864-872).

Comparative Example 10 (C10)

Comparative Example 10 (C10) in FIG. 12 is from the data of Pantera Lux®. The Pantere® data was referred to in the literature (Thrombosis and Haemostasis, 105, 5, 2011, 864-872).

Comparative Example 11 (C11)

Comparative Example 11 (C11) in FIG. 12 is a non-drug coated balloon of which the surface is not coated with a drug. A balloon catheter (manufactured by Terumo Corp., the material of the balloon (dilation portion) is a nylon elastomer) having a size of a diameter 3.0×a length 20 mm (dilation portion) when dilated was prepared.

1. Method (1) A guiding catheter with a guide wire was inserted by an 8 Fr sheath, and guided to the left and right coronary artery opening portion under X-ray fluoroscopy.

(2) Angiography of each coronary artery was performed (coronary artery: left anterior descending coronary artery (LAD), right coronary artery (RCA), and left circumflex coronary artery (LCX)), and a diameter of coronary artery obtained by angiography was measured by a QCA software.

(3) A site in which a diameter of a stent is 1.2 times, and a diameter of the drug eluting balloon is 1.3 times with respect to a diameter of a blood vessel was selected, and work after stent placement was performed.

(4) After a bare metal stent (BMS) having a diameter of 3 mm and a length 15 mm was dilated for 30 seconds in the selected coronary artery is to give the diameter of the stent 1.2 times larger than the original, a balloon catheter for the stent placement was removed. At the stent placement site, after the drug eluting balloon (balloon diameter 3 mm×length 20 mm) having the drug coating layer prepared in Example 10 and Comparative Example 6-b (C6-b) and a non-drug coated balloon in Comparative Example 11 (C11) were dilated for 1 minute so as to be 1.3 times with respect to the diameter of a blood vessel, the balloon catheter was removed.

(5) After the drug eluting balloon was dilated, the guiding catheter and the sheath were removed. After a central side of a carotid artery was ligated, a gap of dissected muscles of an incision opening of cervical region was sutured with a suture, and the skin was sutured by a surgical stapler.

(6) 28 days after the balloon dilatation, autopsy was performed.

Calculation Method of Intravascular Stenosis Rate

An intravascular stenosis rate was calculated in according to the following procedure.

Blood vessel images were taken by a Leica microscope and a pathology imaging system. By these images, the internal area of an external elastic lamina area, internal elastic lamina area, internal area of lumen, and internal area of stent were measured.

[Area Stenosis Rate (%) Calculation Method]

Area stenosis rate (%) was calculated from "area stenosis rate=(neointimal area/internal elastic lamina area)×100".

2. Result

FIG. 12 is a graph showing percent area stenosis at 28 days of Example 10 and of Comparative Examples C6-b to C8-b, C10 and C11 for the intravascular stenosis inhibitory effect in porcine coronary arteries. In FIG. 12, the horizontal axis represents Example or Comparative Examples, the numbers "10" means Example 10, and the numbers with letters, that is, "C6-b" to "C8-b", "C10" and "C11" mean Comparative Example 6-b (C6-b), Comparative Example 7-b (C7-b), Comparative Example 8-b (C8-b), Comparative Example 10 (C10) and Comparative Example 11 (C11). In addition, the vertical axis represents percent area stenosis at 28 days.

In Comparative Example 11 (C11), area stenosis rate of a blood vessel treated with the non-drug coated balloon as a non-drug treated control was 38.4%. The area stenosis rate of a blood vessel treated with the drug eluting balloon in Example 10 was 16.8%, and a significant stenosis inhibitory effect was observed as compared to the non-drug treated control. On the other hand, the area stenosis rate of a blood vessel treated with the commercially available drug eluting balloon (IN.PACT®) in Comparative Example 6-b (C6-b) was 30%. That is, the area stenosis rate of a blood vessel treated with the drug eluting balloon according to Example 10 showed a stronger effect than the IN.PACT® of Comparative Example 6-b (C6-b) and any other drug eluting balloons which were referred to the literature, and the most excellent stenosis inhibitory effect was obtained.

J. Morphological Evaluation in a Porcine Coronary Artery (Evaluation of Local Toxicity)

For the drug eluting balloon in Example 10 and a non-drug coated balloon in Comparative Example 11 (C11), morphological analysis of the treated sections in a porcine coronary artery was performed as in evaluation of local toxicity on the blood vessel in according to the following procedure.

1. Method (1) A guiding catheter with a guide wire was inserted by an 8 Fr sheath, and guided to the left and right coronary artery opening portion under X-ray fluoroscopy.

(2) Angiography of each coronary artery was performed (coronary artery: left anterior descending coronary artery (LAD), right coronary artery (RCA), and left circumflex coronary artery (LCX)), and a diameter of coronary artery obtained by angiography was measured by a QCA software.

(3) A site in which a diameter of the drug eluting balloon is 1.3 times with respect to a diameter of a blood vessel was selected, and procedure was performed.

(4) After the drug eluting balloon (balloon diameter 3 mm×length 20 mm) having the drug coating layer prepared in Example 10 and a non-drug coated balloon in Comparative Example 11 (C11) were dilated for 1 minute so as to be 1.3 times with respect to the diameter of a blood vessel, the balloon catheter was removed.

(5) After the drug eluting balloon was dilated, the guiding catheter and the sheath were removed. After a central side of a carotid artery was ligated, a gap of dissected muscles of an incision opening of cervical region was sutured with a suture, and the skin was sutured by a surgical stapler.

(6) 28 days after the balloon dilatation, autopsy was performed.

[Injury Score Calculation Method, Injury Score]

Evaluation of injury score was performed in all circumferences of blood vessel according to the method of Schwartz R S., et al. (Schwartz R S., et al. Restenosis and the proportional neointimal response to coronary artery injury: results in a porcine model. J Am Coll Cardiol. 1992, 267-74).

The contents of injury score are as follows.

Score 0: Internal elastic lamina intact; endothelium typically denuded; media compressed but not lacerated.

Score 1: Internal elastic lamina lacerated; media typically compressed but not lacerated.

Score 2: Internal elastic lacerated; media visibly lacerated: external elastic lamina intact but compressed.

Score 3: External elastic lamina lacerated; typically large lacerations of media extending through the external elastic lamina; coil wires sometimes residing in adventitia.

In addition, all the scores were obtained by calculating the average value of the three locations, that is, a proximal location, a middle location, and a distal location of the stent placement sites for each blood vessel.

[Inflammatory Score Calculation Method, Inflammatory Score]

Evaluation of inflammatory score was performed in all circumferences of blood vessel according to the method of Kornowski R., et al. (Kornowski R., et al. In-stent restenosis: contributions of inflammatory responses and arterial injury to neointimal hyperplasia. J Am Coll Cardiol. 1998, 224-230).

The contents of inflammatory score are as follows.

Score 0: No inflammatory cells surrounding the strut.

Score 1: Light, noncircumferential lymphohistocytic infiltrate surrounding the strut.

Score 2: Localized, moderate to dense cellular aggregate surrounding the strut noncircumferentially.

Score 3: Circumferential dense lymphohistiocytic cell infiltration of the strut.

In addition, all the scores were obtained by calculating the average value of the three locations, that is, a proximal location (proximal portion), a middle location (middle portion), and a distal location (distal portion) of the stent placement sites for each blood vessel.

[Fibrin Content Calculation Method, Fibrin Content Score]

Evaluation of fibrin content was performed in all circumferences of blood vessel according to the method of Radke, P. W. et. al (Radke, P. W. et. al Vascular effects of paclitaxel following drug-eluting balloon angioplasty in a porcine coronary model: the importance of excipients. Euro Intervention, 2011; 7, 730-737.

The content of the score of fibrin content is as follows.

Score 0: Fibrin localized in a blood vessel was not observed.

Score 1: Fibrin localized in a blood vessel was observed, or fibrin is moderately deposited in a region less than 25% of all circumferences of blood vessel observable near a strut of the stent.

Score 2: Fibrin is moderately deposited in a region greater than 25% of all circumferences of blood vessel observable, or fibrin is heavily deposited in a region less than 25% of all circumferences of blood vessel observable between the struts and the proximity of the strut.

Score 3: Fibrin is severely deposited in a region greater than 25% of all circumferences of blood vessel observable.

In addition, all the scores were obtained by calculating the average value of the three locations, that is, a proximal location, a middle location, and a distal location of the stent placement sites for each blood vessel.

[Endothelialization Score Calculation Method, Endothelialization Score]

The content of an endothelialization score is as follows.

Score 1: Up to 25% of all circumferences of vascular lumen observable is covered with endothelial cells.

Score 2: 25% to 75% of all circumferences of vascular lumen observable is covered with endothelial cells.

Score 3: Equal to or greater than 75% of all circumferences of vascular lumen observable is covered with endothelial cells.

In addition, all the scores were calculated as an average value of three locations, that is, a proximal, a middle and a distal location to the stent placement site, for each blood vessel.

2. Result

As the local toxicity of the treated sections in a porcine coronary artery, injury score, inflammation score, fibrin content score and endothelialization score were observed. The results are shown in Table 6. Moreover, the larger the number of the injury score is, the larger the injury is, which is not preferable. The larger the number of the inflammation score is, the larger the inflammation, which is not preferable. The larger the number of the fibrin content score is, the larger the fibrin content is, which is not preferable. On the other hand, the smaller the number of the endothelialization score is, the less the blood vessel is covered with the endothelial cells, which is not preferable. In Table 6, 10 in a column of Examples/Comparative Examples is an Example, and C11 is a Comparative Example.

The injury score, the inflammation score, the fibrin content score and endothelialization score of a blood vessel treated with the non-drug coated balloon as a non-drug treated control in Comparative Example 11 (C11) do not have an influence on the vascular remodeling since there is no effect (toxicity) by drugs, and the scores were 0.00±0.00, 0.00±0.00, 1.00±0.00 and 3.00±0.00, respectively.

The injury score, the inflammation score, the fibrin content score and endothelialization score of a blood vessel treated with the drug eluting balloon according to Example 10 were 0.22±0.43, 0.29±0.48, 0.23±0.24 and 2.89±0.28, respectively, and it was made clear that the local toxicity of the treated sections was the same as that of non-drug coated balloon in Comparative Example 11 (C11), that is, in spite that high stenosis inhibition effect was obtained, the local toxicity was extremely low. These results showed that DEB according to Example 10 had no influence on the vascular remodeling, which reduce the risk of its late thrombosis. Although it strongly inhibits the stenosis, dual anti-platelet therapy (DAPT) expects to be limited for 4 weeks to the same extent that non-drug coated balloon does.

TABLE 6

| Examples/ Comparative Example | Injury score | Inflam-mation score | Fibrin content score | Endothe-lialization score |
|---|---|---|---|---|
| 10 | 0.22 ± 0.43 | 0.29 ± 0.48 | 0.23 ± 0.24 | 2.89 ± 0.28 |
| C11 | 0.00 ± 0.00 | 0.00 ± 0.00 | 0.00 ± 0.00 | 3.00 ± 0.00 |

K. Uniform Stenosis Inhibitory Effect in a Porcine Coronary Artery

For the drug eluting balloon in Example 10, Comparative Example 6-b (C6-b) and Comparative Example 11 (C11), uniformity of intravascular stenosis inhibitory effect in a porcine coronary artery was evaluated according to the following procedure.

1. Method

Evaluation of intravascular stenosis inhibitory effect in a porcine coronary artery was performed as in evaluation of the Example 1. All segments were transected into three pieces, that is proximal portion, middle portion and distal portion, and area stenosis rate (%) of segment-to-segment was calculated by histomorphometric analysis.

2. Result

Figure 13:
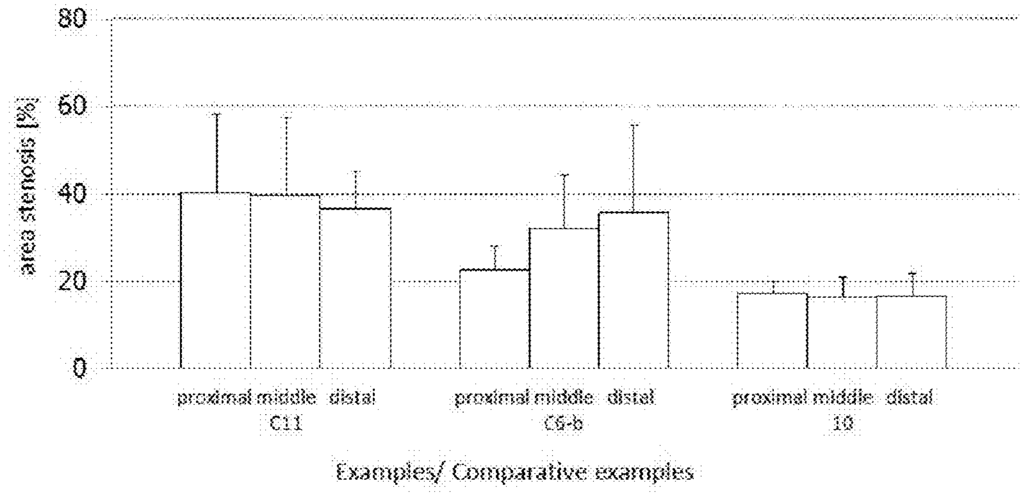
FIG. 13 is a graph showing uniformity of area stenosis rate (%) at 28 days of Example 10, Comparative Examples C6-b and C11 for the intravascular stenosis inhibitory effect in porcine coronary arteries.

FIG. 13 is a graph showing uniformity of area stenosis rate (%) at 28 days of Example 10, Comparative Examples C6-b and C11 for the intravascular stenosis inhibitory effect in porcine coronary arteries. In FIG. 13, the horizontal axis represents Example or Comparative Examples, the number “10” means Example 10, and the numbers with letters, that is, “C6-b” and “C11” mean Comparative Example 6-b (C6-b) and Comparative Example 11 (C11). In addition, the vertical axis represents percent area stenosis of segment-to-segment at 28 days.

Drug eluting balloon according to Example 10 provided uniform inhibitory effects of vascular intima thickening in the treated lesion. On the other hand, effects of segment-to-segment in the lesion treated by the commercially available drug eluting balloon (IN.PACT®) according to Comparative Example 6-b (C6-b) were not uniform.

L. Uniformity of Drug Coating Layers on Balloon Surface

For the drug eluting balloon in Examples 10 to 13 and Comparative Example 6-b (C6-b) and Comparative Example 12 (C12), uniformity of drug layers coated on surface of balloon was evaluated according to the following procedure.

Example 11

Preparation of Drug Eluting Balloon

A balloon catheter (manufactured by Terumo Corp., the material of the balloon (dilation portion) is a nylon elastomer) having a size of a diameter 6.0×a length 100 mm (dilation portion) when dilated was prepared.

Coating solution 2 was prepared. The coating solution 2 was coated on the dilated balloon such that the solvent of the coating solution is slowly volatilized to make the amount of paclitaxel be about 3 μg/mm$^2$.

That is, the coating was performed as in the Example 2.

Example 12

Preparation of Drug Eluting Balloon

A balloon catheter (manufactured by Terumo Corp., the material of the balloon (dilation portion) is a nylon elastomer) having a size of a diameter 6.0×a length 200 mm (dilation portion) when dilated was prepared.

Coating solution 2 was prepared. The coating solution 2 was coated on the dilated balloon such that the solvent of the coating solution is slowly volatilized to make the amount of paclitaxel be about 3 μg/mm$^2$.

That is, the coating was performed as in the Example 2.

Example 13

Preparation of Drug Eluting Balloon

A balloon catheter (manufactured by Terumo Corp., the material of the balloon (dilation portion) is a nylon elastomer) having a size of a diameter 7.0×a length 200 mm (dilation portion) when dilated was prepared.

Coating solution 2 was prepared. The coating solution 2 was coated on the dilated balloon such that the solvent of the coating solution is slowly volatilized to make the amount of paclitaxel be about 3 μg/mm$^2$.

That is, the coating was performed as in the Example 2.

Comparative Example 12 (C12)

IN.PACT® (manufactured by INVAtec/Medtronic, Inc.) was provided. The balloon having a size of a diameter 7.0×a length 120 mm (dilation portion) when dilated was prepared.

1. Method

For drug eluting balloons in Examples 11 to 13 and Comparative Example C12 (C12), that is having a size of a length 100 to 200 mm, uniformity analysis of drug layers on balloon surface was performed by cutting into 20 mm segments. On the other hand, drug eluting balloons in Example 10 and Comparative Example C6-b (C6-b), that is having a size of a length 20 mm, were cut into 6 or 7 mm segments. The paclitaxel content of segment-to-segment on balloon surface was measured by high performance liquid chromatography.

2. Result

As the uniform evaluation of drug coating layers, the paclitaxel content of segment-segment on balloon surface was analyzed. The results are shown in Table 7. In Table 7, “10” to “13” in a column of Examples/Comparative Examples are Examples, and “C6-b” and “C12” are Comparative Examples.

Drug eluting balloon having a size of a length 20 mm in Example 10 was cut into 6 or 7 mm segments, and then it showed relative standard deviation (RSD %) of paclitaxel content of segment-to-segment was 13.0(%). On the other hand, the drug eluting balloon having a size of a length 20 mm in Comparative Example C6-b (C6-b) was cut into 6 or 7 mm segments in the same way, and then it showed relative standard deviation (RSD %) of paclitaxel content was 22.8%. That is, the drug eluting balloon as described herein has more uniform drug coating layers than that of Comparative Example C6-b.

In addition, drug elution balloon having a size of a length 100 to 200 mm in Examples 11 to 13 was cut into 20 mm segments, and then relative standard deviation (RSD %) of paclitaxel content of segment-to-segment was 1.0-3.4(%). On the other hand, the drug eluting balloon having a size of a length 120 mm in Comparative Example C12 (C12) was cut into 20 mm segment in the same way, and then relative standard deviation (RSD %) of paclitaxel content was 25.3%. That is, it was showed that the drug eluting balloon as described herein has a uniform drug coating layer regardless of length of the balloon. In addition, it was showed the drug coating layer is significant uniform compared to IN.PACT.

TABLE 7

| Examples/ Comparative Examples | Balloon size | RSD (%) |
|---|---|---|
| 10 | ϕ3-20 mm | 13.0 |
| 11 | ϕ6-100 mm | 1.0 |
| 12 | ϕ6-200 mm | 3.4 |
| 13 | ϕ7-200 mm | 1.7 |
| C6-b | ϕ3-20 mm | 22.8 |
| C12 | ϕ7-120 mm | 25.3 |

M. Observation of Drug Coating Layer Uniformity of Drug Eluting Balloon by Scanning Electron Microscope (SEM)

For drug coating layer uniformity of drug eluting balloon in Example 10 and Comparative Example 6-b (C6-b), paclitaxel crystals of drug coating layer was observed by scanning electron microscope (SEM).

1. Method

Observation of drug coating layer uniformity of drug eluting balloon by scanning electron microscope (SEM) was performed as in SEM images of drug eluting balloon in Examples 1 to 6 (FIGS. 1 to 6).

2. Result

Figure 14:
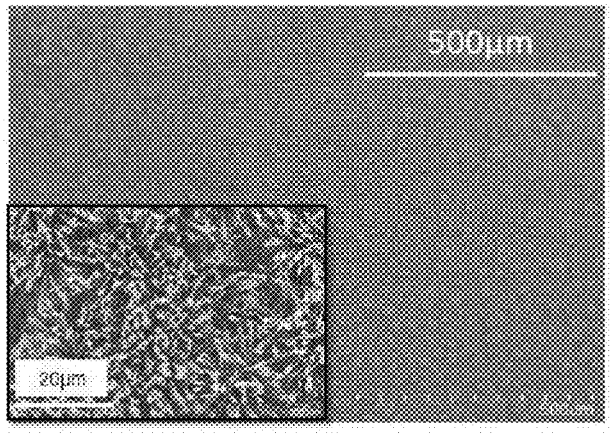
FIG. 14 is scanning electron microscope images of Example 10, showing uniform paclitaxel micro-crystals.
Figure 15:
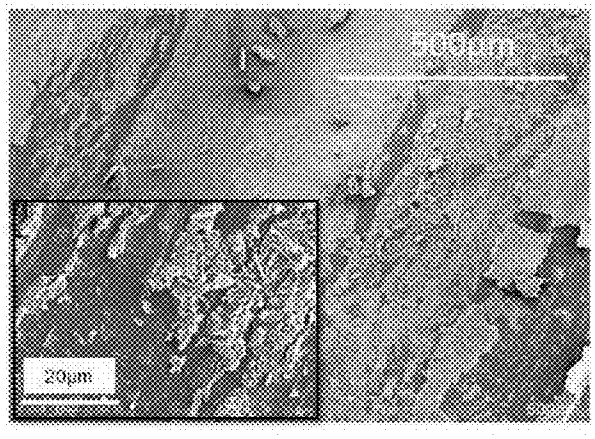
FIG. 15 is scanning electron microscope images of Comparative Example C6-b (C6-b), showing a non-uniform drug coating layer.

As the uniformity of drug coating layers, paclitaxel crystals of drug coating layer were observed. The SEM images shown in FIG. 14 and FIG. 15 were obtained. FIG. 14 is SEM images of Example 10, and FIG. 15 is SEM images of Comparative Example C6-b (C6-b).

FIG. 14, which is SEM images of Example 10, showed uniform paclitaxel micro-crystals. In addition, it was shown that the paclitaxel micro-crystals uniformity arranged and constantly sized in the drug coating layer on the balloon surface. On the other hand, FIG. 15, which is SEM images of Comparative Example C6-b (C6-b), showed non-uniform drug coating layer. In addition, SEM images of FIG. 15, which is IN.PACT in Comparative Example C6-b (C6-b), showed that drug coating layer is composed of crystals and amorphous material.

N. Evaluation of Durability of Drug Coating Layer on Balloon Surface

For the drug eluting balloon in Examples 13, 14 and Comparative Example 12 (C12), durability of drug coating layers on balloon surface was evaluated according to the following procedure.

Example 14

Preparation of Drug Eluting Balloon

A balloon catheter (manufactured by Terumo Corp., the material of the balloon (dilation portion) is a nylon elastomer) having a size of a diameter 6.0×a length 40 mm (dilation portion) when dilated was prepared.

Coating solution 2 was prepared. The coating solution 2 was coated on the dilated balloon such that the solvent of the coating solution is slowly volatilized to make the amount of paclitaxel be about 3 $\mu g/mm^2$.

That is, the coating was performed as in the Example 2.

1. Method

To measure durability of drug coating layer during a process to be delivered to the lesion of the treatment, the test was performed using a simulated peripheral model. The guiding sheath was filled with normal saline and was set having an angle of about 45 degrees. And then, a guide wire was passed through the guiding sheath. During the test, normal saline in the guiding sheath was kept at 37° C. Drug eluting balloon was tracked over a guide wire for 1 minute until the balloon exited. After that, the residual paclitaxel content on balloon surface was measured by high performance liquid chromatography.

2. Result

As the durability evaluation of drug coating layers, residual paclitaxel content on balloon surface after the passage in a simulated peripheral model was measured. The results are shown in Table 8. In Table 8, "13" and "14" in a column of Examples/Comparative Examples are Examples, and "C12" is a Comparative Example.

After simulated use in wet vessel model, residual paclitaxel content on balloon surface of drug eluting balloon having a size of a length 40 mm in Example 14 was 84% (before inflation). In addition, residual paclitaxel content on balloon surface of drug eluting balloon having a size of a length 200 mm in Example 13 was 84%. On the other hand, residual paclitaxel content of the IN.PACT having a size of a length 120 mm in Comparative Example C12 (C12) was 63%. It was shown that the drug eluting balloon as described herein can deliver paclitaxel while applying uniform microcrystals to the entire treated lesion. In addition, the drug eluting balloon with long length can keep the uniform microcrystalline drug during delivering to the target lesion, too. In other words, the distal portion, the middle portion, and the proximal portion of the drug eluting balloon were able to circumferentially maintain a uniform structure of the plurality of the regularly arranged crystals on the balloon after delivery to the lesion to be treated. Especially, the distal end (the distal portion) of the expandable member (balloon) is mostly slided or glided to other surfaces including the lumen of the medical devices like catheters, and the structure of the uniform crystalline particles on the balloon can easily come off. Therefore, the distal end of the expandable member as described herein has a drug coating layer which shows an inhibitory effects of vascular intima thickening.

Based on what has been described above, it was made clear that drug eluting balloon as described herein can deliver the uniform paclitaxel micro-crystals without comeoff (detachment or falling away) from the balloon surface during a process to be delivered to the lesion of the treatment. That is, the drug eluting balloon as described herein can be expanded in the lesion of the treatment while keeping the uniformity of the drug coating layer until dilated.

TABLE 8

| Examples/ Comparative Example | Balloon size | Residual paclitaxel content on the balloon surface after the passage in wet vessel model |
|---|---|---|
| 14 | ϕ6-40 mm | 84% |
| 13 | ϕ7-200 mm | 84% |
| C12 | ϕ7-120 mm | 63% |

O. Pharmacokinetics in Porcine Ilio-Femoral Arteries 2

For the drug eluting balloon in Example 9, Comparative Example 6-a (C6-a), Comparative Example 7-a (C7-a) and Comparative Example 13 (C13), pharmacokinetics in porcine iliofemoral arteries was evaluated according to the following procedure.

Comparative Example 13 (C13)

Figure 16:
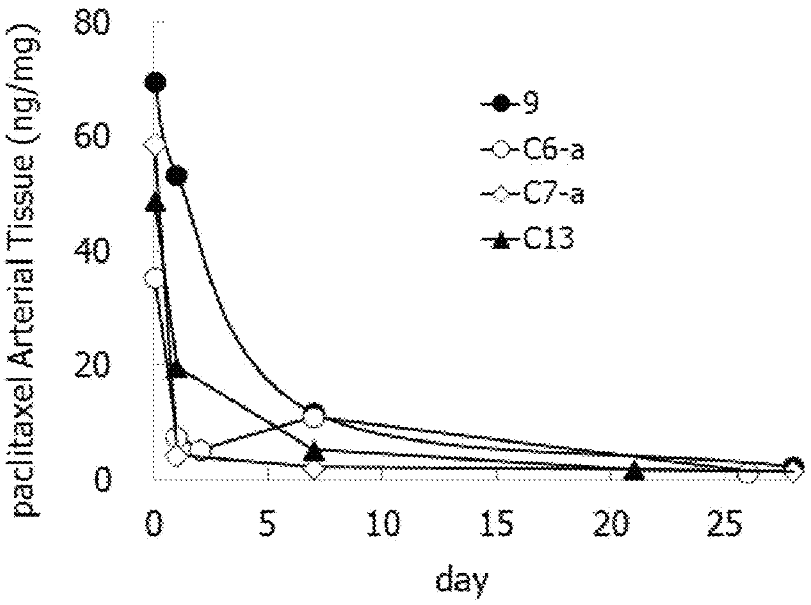
FIG. 16 is a graph showing the pharmacokinetic profile of Example 9, Comparative Example 6-a (C6-a), Comparative Example 7-a (C7-a) and Comparative Example 13 (C13) for the transfer in the porcine femoral arterial tissue.
Figure 17:
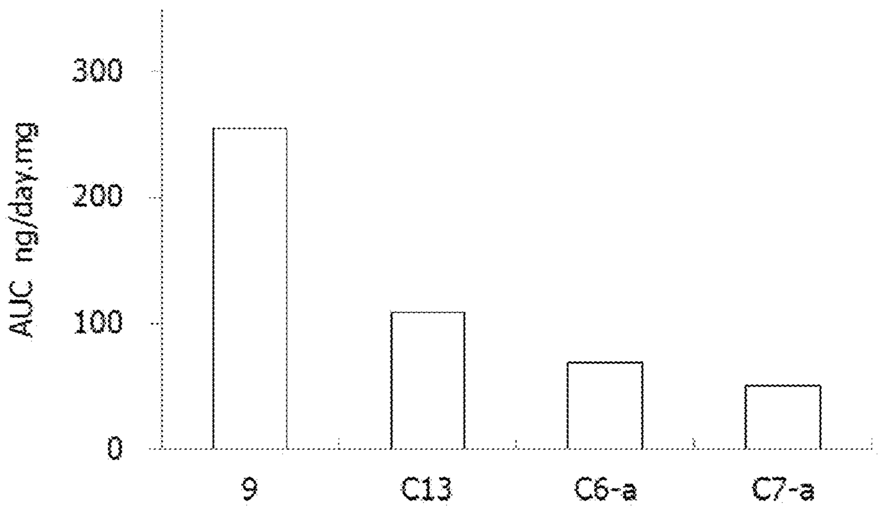
FIG. 17 is a graph showing the AUC of the drug of Example 9, Comparative Example 6-a (C6-a), Comparative Example 7-a (C7-a) and Comparative Example 13 (C13) for the transfer in the porcine femoral arterial tissue.

Comparative Example 13 (C13) in FIG. 16 and FIG. 17 is the Ranger™ (manufactured by Boston Scientific) which is a paclitaxel-coated balloon catheter. The Ranger™ results were disclosed on the web site by Boston Scientific.

1. Method

Pharmacokinetics was performed as in the method of "H".

The target tissue was carefully dissected from surrounding tissue following treatment with the drug eluting balloon. The paclitaxel concentration measurement in tissue was performed by LC-MS/MS analysis.

2. Result

Pharmacokinetics in porcine femoral arteries was evaluated. FIG. 16 is a graph showing the pharmacokinetic profile of Example 9, Comparative Example 6-a (C6-a), Comparative Example 7-a (C7-a) and Comparative Example 13 (C13) for the transfer in the porcine femoral arterial tissue. The horizontal axis represents day(s) after dilation of the drug eluting balloon. In addition, the vertical axis represents drug concentration in the target arterial tissue. In FIG. 17, the horizontal axis represents Example or Comparative Examples, the number "9" means Example 9, and the numbers with letters, that is, "C6-a", "C7-a", and "C13" mean Comparative Example 6-a (C6-a), Comparative Example 7-a (C7-a) and Comparative Example 13 (C13), respectively. In addition, the vertical axis represents the AUC (ng·day/mg) of drug on 0.02 day to 7 days in the target arterial tissue.

As illustrated in FIG. 16, the drug concentration in the target arterial tissue observed in Example 9 was 69.8, 53.4, 11.7, 4.0, and 2.3 ng/mg tissue on day 0.04, 1, 7, 21, and 28, respectively. On the other hand, the drug concentration in the target arterial tissue observed in Comparative Example 6-a (C6-a) was 35, 7.7, 5.3, 11.1, and 1.5 ng/mg tissue on day 0.02, 1, 2, 7, and 26, respectively. The drug concentration in the target arterial tissue observed in Comparative Example 7-a (C7-a) was 58.9, 4.4, 2.2, and 1.6 ng/mg tissue on day 0.02, 1, 7, and 28, respectively. The drug concentration in the target arterial tissue observed in Comparative Example 13 (C13) was 48.8, 19.8, 5.3, 1.9, and 0.4 ng/mg tissue on day 0.02, 1, 7, and 21, respectively. That is, the reduction rate of drug from 0.04 day (1 hour) to 1 day for Example 9 was at most 50%. On the other hand, the reduction rate of drug from 0.02-0.04 day (0.5-1 hour) to 1 day for Comparative Example 6-a (C6-a), Comparative Example 7-a (C7-a) and Comparative Example 13 (C13) was more than 50%.

FIG. 17 is a graph showing the AUC of the drug on 0.02-0.04 days (0.5-1 hour) to 7 days of Examples 9, Comparative Example 6-a (C6-a), Comparative Example 7-a (C7-a) and Comparative Example 13 (C13) for the transfer in the porcine femoral arterial tissue. In addition, the vertical axis represents the AUC (ng·day/mg) of drug on 0.02-0.04 day to 7 day in the target arterial tissue.

The AUC of the drug on 0.04 day (1 hour) to 7 day in the target arterial tissue after the balloon dilation observed in Example 9 was 254 ng·day/mg. On the other hand, the AUC of the drug on 0.02-0.04 day (0.5-1 hour) to 7 day in the target arterial tissue after the balloon dilation observed in Comparative Example 6-a (C6-a), Comparative Example 7-a (C7-a) and Comparative Example 13 (C13) was 69, 51, and 109 ng·day/mg, respectively. That is, the AUC obtained in Example 9 was higher than 200 ng·day/mg. On the other hand, the AUC obtained in Comparative Example 6-a (C6-a), Comparative Example 7-a (C7-a) and Comparative Examples 13 (C13) was lower than 200 ng·day/mg. The AUC obtained in Example 9 is the highest.

As described herein, a high drug concentration in tissue by day 7 after dilation of the balloon has an effect on smooth muscle cell proliferation. After that, prompt clearance from the tissue does not inhibit endothelial cell growth.

The detailed description above describes a drug coating layer disclosed by way of example. The invention is not limited, however, to the precise embodiment and variations described. Various changes, modifications and equivalents can be employed by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of reducing the risk of embolization of peripheral blood vessels, comprising:

inserting a medical device into one of the peripheral blood vessels, the medical device comprising a polyamide expandable member possessing a polyamide surface on which a drug coating layer is disposed, the drug coating layer being applied to the polyamide surface of the polyamide expandable member by reverse rotation in which the expandable member is rotated in an opposite direction of dispensing the drug coating layer and in which the drug coating layer is dispensed by a dispenser in contact with the polyamide surface of the expandable member, the drug coating layer having a crystalline morphological form including a plurality of crystal particles of a water-insoluble drug regularly arranged and uniformly sized on the polyamide surface of the polyamide expandable member, each of the crystal particles being independently formed on the polyamide surface of the polyamide expandable member, expanding the polyamide expandable member, pressing the drug coating layer to a blood vessel wall of the peripheral blood vessel such that at least part of the plurality of crystal particles is transferred to the blood vessel wall, and deflating the polyamide expandable member such that generation of microparticulates having a size that causes embolization of peripheral blood vessels is suppressed.

2. The method of claim 1, wherein each of the plurality of crystal particles has an elongated body with a linearly-shaped long axis and forms an angle in a predetermined range with respect to the polyamide surface of the polyamide expandable member with which the long axis of the elongated body intersects.

3. The method of claim 2, wherein at least a vicinity of a distal end of the elongated body is hollow.

4. The method of claim 2, wherein a cross-sectional shape of the elongated body perpendicular to the long axis is a polygon.

5. The method of claim 1, wherein the drug coating layer which has the crystalline morphological form including the plurality of crystal particles of water-insoluble drug comprises excipient particles formed of an excipient which are irregularly arranged between the crystal particles; and wherein a molecular weight of the excipient is less than a molecular weight of the water-insoluble drug, a ratio occupied by the excipient particles per a predetermined area of the substrate is less than a ratio occupied by the crystal particles, and the excipient particles do not form a matrix.

6. The method of claim 1, wherein the water-insoluble drug is selected from a group consisting of paclitaxel, rapamycin, docetaxel, and everolimus.

7. The method of claim 1, wherein microparticulates are generated in the blood vessels.

8. The method of claim 7, wherein the microparticulates generated in the blood vessels have a diameter of 10-25 μm.

9. The method of claim 1, further comprising lowering a level of necrosis.

10. The method of claim 1, further comprising lowering a risk of amputation.

11. The method of claim 1, wherein the suppression of the generation of microparticulates having a size that causes embolization of peripheral blood vessels includes suppressing microparticulates of a diameter of 100 μm to 900 μm.

12. The method of claim 1, wherein the drug coating layer is dispensed by the dispenser while the dispenser translates along a longitudinal axis of the medical device at a speed of 0.01 mm/sec 2 mm/sec.

13. The method of claim 1, wherein the drug coating layer is dispensed on the polyamide surface of the expandable member at 0.01 μL/sec 1.5 μL/sec.

14. A method of reducing the risk of embolization of peripheral blood vessels, comprising:

inserting a medical device into one of the peripheral blood vessels, the medical device comprising a polyamide expandable member possessing a polyamide surface on which a drug coating layer is disposed, the drug coating layer being applied to the polyamide surface of the polyamide expandable member by reverse rotation in which the expandable member is rotated in an opposite direction of dispensing the drug coating layer and in which the drug coating layer is dispensed by a dispenser in contact with the polyamide surface of the expandable member, the drug coating layer having a crystalline morphological form and comprising: a plurality of crystal particles of a water-insoluble drug; a solvent in which the plurality of crystal particles are dissolved, the solvent being comprised of water and at least one of tetrahydrofuran and acetone; and excipient particles formed of an excipient irregularly arranged between the crystal particles, a molecular weight of the excipient being less than a molecular weight of the water-insoluble drug, the crystal particles being regularly arranged and uniformly sized on the polyamide surface of the polyamide expandable member, each of the crystal particles being independently formed on the polyamide surface of the polyamide expandable member, expanding the expandable member, pressing the drug coating layer to a blood vessel wall such that at least part of the plurality of crystal particles is transferred to the blood vessel wall, and deflating the expandable member such that generation of microparticulates having a size that causes embolization of peripheral blood vessels is suppressed.

15. The method of claim 14, wherein each of the plurality of crystal particles is an elongated body and at least a vicinity of a distal end of each elongated body is hollow.

16. The method of claim 14, wherein each of the plurality of crystal particles is an elongated body possessing a long axis, and a cross-sectional shape of each elongated body perpendicular to the long axis is a polygon.

17. The method of claim 14, wherein the drug coating layer is dispensed by the dispenser while the dispenser translates along a longitudinal axis of the medical device at a speed of 0.01 mm/sec-2 mm/sec.

18. The method of claim 14, wherein the drug coating layer is dispensed on the polyamide surface of the expandable member at 0.01 μL/sec-1.5 μL/sec.

19. A method of reducing the risk of embolization of peripheral blood vessels, comprising:

inserting a medical device into one of the peripheral blood vessels, the medical device comprising a polyamide expandable member possessing a polyamide surface on which a drug coating layer is disposed, the drug coating layer being applied to the polyamide surface of the polyamide expandable member by reverse rotation in which the expandable member is rotated in an opposite direction of dispensing the drug coating layer and in which the drug coating layer is dispensed by a dispenser in contact with the polyamide surface of the expandable member, the drug coating layer having a crystalline morphological form and comprising: a plurality of crystal particles of a water-insoluble drug; a solvent in which the plurality of crystal particles are dissolved, the solvent being comprised of water and at least one of tetrahydrofuran and acetone; and excipient particles formed of an excipient irregularly arranged between the crystal particles, a molecular weight of the excipient being less than a molecular weight of the water-insoluble drug, the crystal particles of the water-insoluble drug each defining an elongated body, the elongated bodies forming the crystal particles each possessing one end fixed to the polyamide expandable member, the elongated bodies forming the crystal particles being regularly arranged and uniformly sized on the polyamide surface of the polyamide expandable member, each of the elongated bodies forming the crystal particles being independently formed on the polyamide surface of the polyamide expandable member, each of the elongated bodies forming the crystal particles possessing a long axis that intersects the polyamide surface of the polyamide expandable member, expanding the expandable member, pressing the drug coating layer to a blood vessel wall such that at least part of the plurality of crystal particles is transferred to the blood vessel wall, and deflating the expandable member such that generation of microparticulates having a size that causes embolization of peripheral blood vessels is suppressed.

20. The method of claim 19, wherein a vicinity of a distal end of each elongated body is hollow.

21. The method of claim 19, wherein a cross-sectional shape of each elongated body perpendicular to the long axis is a polygon.

22. The method of claim 19, wherein the drug coating layer is dispensed by the dispenser while the dispenser translates along a longitudinal axis of the medical device at a speed of 0.01 mm/sec-2 mm/sec.

23. The method of claim 19, wherein the drug coating layer is dispensed on the polyamide surface of the expandable member at 0.01 μL/sec-1.5 μL/sec.

24. A method of reducing the risk of embolization of peripheral blood vessels, comprising:

inserting a medical device into one of the peripheral blood vessels, the medical device comprising an expandable member possessing a surface on which a drug coating layer is disposed, the drug coating layer being applied to the surface of the expandable member by reverse rotation in which the expandable member is rotated in an opposite direction of dispensing the drug coating layer and in which the drug coating layer is dispensed by a dispenser in contact with the surface of the expandable member, the drug coating layer having a crystalline morphological form including a plurality of crystal particles of a water-insoluble drug regularly arranged and uniformly sized on the surface of the expandable member, each of the crystal particles being formed on the surface of the expandable member, expanding the expandable member, pressing the drug coating layer to a blood vessel wall of the peripheral blood vessel such that at least part of the plurality of crystal particles is transferred to the blood vessel wall, and deflating the expandable member such that generation of microparticulates having a size that causes embolization of peripheral blood vessels is suppressed.

25. The method of claim 24, wherein the drug coating layer is dispensed by the dispenser while the dispenser translates along a longitudinal axis of the medical device at a speed of 0.01 mm/sec-2 mm/sec.

26. The method of claim 24, wherein the drug coating layer is dispensed on the surface of the expandable member at 0.01 μL/sec-1.5 μL/sec.

* * * * *